US010743750B2

(12) United States Patent
Hunter et al.

(10) Patent No.: US 10,743,750 B2
(45) Date of Patent: Aug. 18, 2020

(54) MULTI-LINK MODULAR CONTINUUM ROBOTIC ENDOSCOPE SYSTEM

(71) Applicant: Massachusetts Institute of Technology, Cambridge, MA (US)

(72) Inventors: Ian W. Hunter, Lincoln, MA (US); Yi Chen, St. Charles, MO (US); Jiahui Liang, Chicago, IL (US)

(73) Assignee: Massachusetts Institute of Technology, Cambridge, MA (US)

( * ) Notice: Subject to any disclaimer, the term of this patent is extended or adjusted under 35 U.S.C. 154(b) by 477 days.

(21) Appl. No.: 15/307,596

(22) PCT Filed: Apr. 28, 2015

(86) PCT No.: PCT/US2015/028082
§ 371 (c)(1),
(2) Date: Oct. 28, 2016

(87) PCT Pub. No.: WO2015/168177
PCT Pub. Date: Nov. 5, 2015

(65) Prior Publication Data
US 2017/0049298 A1 Feb. 23, 2017

Related U.S. Application Data

(60) Provisional application No. 61/985,410, filed on Apr. 28, 2014.

(51) Int. Cl.
*A61B 1/00* (2006.01)
*A61B 1/005* (2006.01)
(Continued)

(52) U.S. Cl.
CPC ............ *A61B 1/0055* (2013.01); *A61B 1/005* (2013.01); *A61B 1/00006* (2013.01);
(Continued)

(58) Field of Classification Search
CPC ... A61B 1/0055; A61B 1/00105; A61B 1/008; A61B 1/00006; A61B 1/0016;
(Continued)

(56) References Cited

U.S. PATENT DOCUMENTS 4,869,238 A 9/1989 Opie et al.
5,005,558 A 4/1991 Aomori
(Continued)

FOREIGN PATENT DOCUMENTS

DE 195 22 176 A1 1/1997
DE 102 33 225 A1 2/2004
(Continued)

OTHER PUBLICATIONS

Armacost et al., Accurat and Reproducible Target Navigation with the Stereotaxis Niobe Magnetic Navigation System. J Cardiovasc Electrophysiol. Jan. 2007;18(Suppl. 1):S26-S31.
(Continued)

*Primary Examiner* — Timothy J Neal
(74) *Attorney, Agent, or Firm* — McCarter & English, LLP

(57) ABSTRACT

Robotic endoscopes have the potential to help endoscopists position tools during procedures, to propel the endoscope to the desired position, to automate functions and to prevent perforations during procedures. Modular architecture for a continuum robotic endoscope with multiple bending segments along the length of the endoscope. Each of the segments is modular, containing a set of actuation motors that drive short cables in the continuum segments.

43 Claims, 30 Drawing Sheets

(51) Int. Cl.

| | | |
|---|---|---|
| *A61B 1/008* | (2006.01) | |
| *A61B 1/018* | (2006.01) | |
| *A61B 1/04* | (2006.01) | |
| *A61B 1/31* | (2006.01) | |
| *A61B 5/06* | (2006.01) | |
| *A61B 6/12* | (2006.01) | |
| *A61B 6/00* | (2006.01) | |
| A61B 34/20 | (2016.01) | |
| A61B 34/30 | (2016.01) | |
| A61B 90/00 | (2016.01) | |

(52) U.S. Cl.
CPC ............ *A61B 1/008* (2013.01); *A61B 1/0016* (2013.01); *A61B 1/00045* (2013.01); *A61B 1/0052* (2013.01); *A61B 1/0057* (2013.01); *A61B 1/00105* (2013.01); *A61B 1/018* (2013.01); *A61B 1/04* (2013.01); *A61B 1/31* (2013.01); *A61B 5/067* (2013.01); *A61B 6/12* (2013.01); *A61B 6/487* (2013.01); *A61B 2034/2053* (2016.02); *A61B 2034/301* (2016.02); *A61B 2090/064* (2016.02); *A61B 2562/0261* (2013.01)

(58) Field of Classification Search
CPC ......... A61B 1/0057; A61B 1/04; A61B 1/018; A61B 1/00052; A61B 1/31; A61B 1/00045; A61B 5/067; A61B 6/12; A61B 6/487; A61B 2090/064
See application file for complete search history.

(56) References Cited

U.S. PATENT DOCUMENTS

| | | | |
|---|---|---|---|
| 5,060,632 A * | 10/1991 | Hibino | A61B 1/00039 |
| | | | 348/65 |
| 5,337,732 A | 8/1994 | Grundfest et al. | |
| 5,341,240 A | 8/1994 | Broome | |
| 5,347,989 A | 9/1994 | Monroe et al. | |
| 5,396,879 A | 3/1995 | Wilk et al. | |
| 5,469,840 A | 11/1995 | Tanii et al. | |
| 5,489,256 A | 2/1996 | Adair | |
| 5,630,782 A | 5/1997 | Adair | |
| 5,643,175 A | 7/1997 | Adair | |
| 5,662,587 A | 9/1997 | Grundfest et al. | |
| 5,688,221 A | 11/1997 | Yabe et al. | |
| 5,704,898 A | 1/1998 | Kokish | |
| 5,817,015 A | 10/1998 | Adair | |
| 5,833,605 A | 11/1998 | Shah | |
| 5,857,964 A | 1/1999 | Konstorum et al. | |
| 5,873,814 A | 2/1999 | Adair | |
| 6,013,024 A | 1/2000 | Mitsuda et al. | |
| 6,066,090 A | 5/2000 | Yoon | |
| 6,081,740 A | 6/2000 | Gombrich et al. | |
| 6,425,870 B1 | 7/2002 | Flesch | |
| 6,468,203 B2 | 10/2002 | Belson | |
| 6,605,036 B1 | 8/2003 | Wild | |
| 6,610,007 B2 * | 8/2003 | Belson | A61B 1/0053 |
| | | | 600/146 |
| 6,638,213 B2 | 10/2003 | Ogura et al. | |
| 6,908,428 B2 | 6/2005 | Aizenfeld et al. | |
| 7,056,283 B2 | 6/2006 | Baror et al. | |
| 7,087,013 B2 | 8/2006 | Belson et al. | |
| 7,413,543 B2 | 8/2008 | Banik et al. | |
| 7,491,166 B2 | 2/2009 | Ueno et al. | |
| 7,578,786 B2 | 8/2009 | Boulais et al. | |
| 7,591,783 B2 | 9/2009 | Boulais et al. | |
| 7,666,135 B2 | 2/2010 | Couvillon, Jr. | |
| 7,722,532 B2 | 5/2010 | Ikeda et al. | |
| 7,727,186 B2 | 6/2010 | Makower et al. | |
| 7,828,723 B2 | 11/2010 | Ueno et al. | |
| 8,248,413 B2 | 8/2012 | Gattani et al. | |
| 8,443,692 B2 | 5/2013 | Zubiate et al. | |
| 8,610,765 B2 | 12/2013 | Yamaguchi | |
| 2002/0123664 A1 | 9/2002 | Mitsumori | |
| 2003/0045778 A1 * | 3/2003 | Ohline | A61B 1/0053 |
| | | | 600/114 |
| 2003/0130564 A1 | 7/2003 | Martone et al. | |
| 2004/0138525 A1 | 7/2004 | Saadat et al. | |
| 2004/0186350 A1 | 9/2004 | Brenneman et al. | |
| 2004/0199052 A1 | 10/2004 | Banik et al. | |
| 2005/0119527 A1 | 6/2005 | Banik et al. | |
| 2005/0240078 A1 | 10/2005 | Kwon et al. | |
| 2005/0282648 A1 | 12/2005 | Kim | |
| 2006/0041188 A1 | 2/2006 | Dirusso et al. | |
| 2006/0094933 A1 | 5/2006 | Goldfarb et al. | |
| 2007/0161861 A1 | 7/2007 | Kawai et al. | |
| 2007/0173694 A1 | 7/2007 | Tsuji et al. | |
| 2008/0071142 A1 * | 3/2008 | Gattani | A61B 1/0005 |
| | | | 600/117 |
| 2008/0119695 A1 | 5/2008 | Ueno et al. | |
| 2008/0200763 A1 | 8/2008 | Ueno | |
| 2009/0030562 A1 * | 1/2009 | Jacobsen | B08B 9/045 |
| | | | 701/2 |
| 2009/0099420 A1 | 4/2009 | Woodley et al. | |
| 2009/0099551 A1 * | 4/2009 | Tung | A61B 5/103 |
| | | | 604/530 |
| 2009/0171161 A1 * | 7/2009 | Ewers | A61B 1/0052 |
| | | | 600/149 |
| 2009/0216083 A1 | 8/2009 | Durant et al. | |
| 2010/0069719 A1 | 3/2010 | Wehrheim | |
| 2010/0160730 A1 | 6/2010 | Konomura | |
| 2010/0268031 A1 | 10/2010 | Koyama | |
| 2010/0274087 A1 | 10/2010 | Diolaiti et al. | |
| 2012/0084108 A1 | 4/2012 | Bohannon et al. | |
| 2012/0157771 A1 | 6/2012 | Avitsian et al. | |
| 2012/0220830 A1 | 8/2012 | Yang et al. | |
| 2013/0012821 A1 * | 1/2013 | Lin | A61B 34/73 |
| | | | 600/473 |
| 2014/0330432 A1 * | 11/2014 | Simaan | B25J 9/1633 |
| | | | 700/250 |
| 2015/0011830 A1 | 1/2015 | Hunter et al. | |

FOREIGN PATENT DOCUMENTS

| | | |
|---|---|---|
| EP | 0587506 A1 | 3/1994 |
| EP | 1481628 B1 | 7/2009 |
| JP | H0482529 A | 3/1992 |
| JP | H16114001 A | 4/1994 |
| JP | 2000014628 A | 1/2000 |
| WO | 2004019769 A1 | 3/2004 |
| WO | 2009097461 A1 | 8/2009 |
| WO | 2010149969 A1 | 12/2010 |
| WO | 2012027581 A2 | 3/2012 |
| WO | 2015/168177 A1 | 11/2015 |

OTHER PUBLICATIONS

Bardou et al., Design of telemanipulated system for transluminal surgery. 31st Annual International Conference of the IEEE EMBS. pp. 5577-5582, Sep. 2009.

Bethea et al., Application of haptic feedback to robotic surgery. J Laparoendosc Adv Surg Tech A. Jun. 2004;14(3):191-5.

Chen et al., Multi-turn, Tension-stiffening Catheter Navigation System. 2010 IEEE International Conference on Robotics and Automation. pp. 5570-5575, May 2010.

Drewalowski (Ed.), Olympus Observer. The modern magazine for endoscopy from Olympus Medical Systems. Exploiting synergies for a more effective working environment. Systems Integration. Olympus Medical Systems Europa GmbH. www.olympus-europa.com. 48 pages (2008).

Kanagaratnam et al., Experience of robotic catheter ablation in humans using a novel remotely steerable catheter sheath. J Interv Card Electrophysiol. Jan. 2008;21(1):19-26.

Mayer et al., Haptic Feedback in a Terepresence System for Endoscopic Heart Surgery. Presence. Oct. 2007;16(5):459-470.

Oliveira et al., Robotic Endoscope Motor Module and Gearing Design. IEEE EMB Conference. 4 pages, Jun. 20, 2011.

(56) References Cited

OTHER PUBLICATIONS

Phee et al., Master and Slave Transluminal Endoscopic Robot (MASTER) for Natural Orifice Transluminal Endoscopic Surgery (NOTES). 31st Annual International Conference of the IEEE EMBS. pp. 1192-1195, Sep. 2009.

Rosen et al., Force Controlled and Teleoperated Endoscopic Grasper for Minimally Invasive Surgery—Experimental Performance Evaluation. IEEE Transactions on Biomedical Engineering. pp. 1-20, (1999).

Rothstein et al., Disposable, sheathed, flexible sigmoidoscopy: a prospective, multicenter, randomized trial. The Disposable Endoscope Study Group. Gastrointest Endosc. Jun. 1995;41(6):566-72.

Tavakoli et al., Haptic interaction in robot-assisted endoscopic surgery: a sensorized end-effector. Int J Med Robot. Jan. 2005;1(2):53-63.

International Search Report for Application No. PCT/US2011/049167, dated Mar. 9, 2012.

Andruska, Adam M., and Katherine S. Peterson. "Control of a snake-like robot in an elastically deformable channel." IEEE/ASME Transactions on Mechatronics 13.2 (Apr. 2008): 219-227.

Bajo, A., R. E. Goldman, and N. Simaan, "Configuration and joint feedback for enhanced performance of multi-segment continuum robots," Proceedings of the 2011 IEEE International Conference on Robotics and Automation, pp. 2905-2912, May 2011.

Cepolina, F., and R. C. Michelini. "Review of robotic fixtures for minimally invasive surgery." The International Journal of Medical Robotics and Computer Assisted Surgery 1.1 (Apr. 2004): 43-63.

Chen Y., J. M. Oliveira, and I. W. Hunter, "Two-axis bend sensor design, kinematics and control for a continuum robotic endoscope," Proceedings of the 2013 IEEE International Conference on Robotics and Automation, pp. 696-702, May 2013.

Chen, Y., J. M. Oliveira, and I. W. Hunter, "Sensor architecture for a two-actuator robotic endoscope tip," in Proceedings of the 33rd Annual International Conference of the IEEE Engineering in Medicine and Biology Society, pp. 8340-8343, Aug. 2011.

Chen, Yi, Shigehiko Tanaka, and Ian W. Hunter. "Disposable endoscope tip actuation design and robotic platform." 2010 Annual International Conference of the IEEE Engineering in Medicine and Biology. IEEE, Aug. 2010.

Degani, Amir, et al. "Highly articulated robotic probe for minimally invasive surgery." Proceedings of the 2008 30th Annual International Conference of the IEEE Engineering in Medicine and Biology Society. IEEE, Aug. 2008. pp. 3273-3276.

Eickhoff, A., et al. "In vitro evaluation of forces exerted by a new computer-assisted colonoscope (the NeoGuide Endoscopy System)." Endoscopy 38.12 (Dec. 2006): 1224-1229.

Eickhoff, Axel, et al. "Computer-assisted colonoscopy (the NeoGuide Endoscopy System): results of the first human clinical trial ("PACE study")." The American journal of gastroenterology 102.2 (Feb. 2007): 261-266.

Glozman, Daniel, et al. "A self-propelled inflatable earthworm-like endoscope actuated by single supply line." IEEE Transactions on Biomedical Engineering 57.6 (Jun. 2010): 1264-1272.

Hopkins, James K., Brent W. Spranklin, and Satyandra K. Gupta. "A survey of snake-inspired robot designs." Bioinspiration & biomimetics 4.2 (Jan. 2009): 021001.

International Search Report and Written Opinion by the International Searching Authority for International Application No. PCT/US15/28082 dated Aug. 5, 2015.

Jones, Bryan A., and Ian D. Walker. "Kinematics for multisection continuum robots." IEEE Transactions on Robotics 22.1 (Feb. 2006): 43-55.

Kwok, Ka-Wai, et al. "Dimensionality reduction in controlling articulated snake robot for endoscopy under dynamic active constraints." IEEE transactions on robotics 29.1 (Feb. 2013): 15-31.

Liang, Jiahui, "Multi-link robotic endoscope with haptic feedback," Thesis submitted to the Department of Mechanical Engineering of the Massachusetts Institute of Technology in partial fulfillment of the degree of Bachelor of Science of Mechanical Engineering. May 9, 2014. (55 pages).

Ota, Takeyoshi, et al. "A highly articulated robotic surgical system for minimally invasive surgery." The Annals of thoracic surgery 87.4 (Apr. 2009): 1253-1256.

Ozaki, K., et al., "Novel design of rubber tube actuator improving mountability and drivability for assisting colonosocope insertion," Proceedings of the 2011 IEEE International Conference on Robotics and Automation, pp. 3263-3268, IEEE, May 2011.

Peirs, Jan, Dominiek Reynaerts, and Hendrik Van Brussel. "A miniature manipulator for integration in a self-propelling endoscope." Sensors and Actuators A: Physical 92.1 (Aug. 2001): 343-349.

Renda, F. and C. Laschi, "A general mechanical model for tendon-driven continuum manipulators," Proceedings of the 2012 IEEE International Conference on Robotics and Automation, pp. 3813-3818, May 2012.

Valdastri, Pietro, Massimiliano Simi, and Robert J. Webster III. "Advanced technologies for gastrointestinal endoscopy." Annual review of biomedical engineering 14 (May 22, 2012): 397-429.

Walker, I., "Continuous backbone 'continuum' robot manipulators," ISRN Robotics, vol. 2013, p. 726506, Jun. 2013.

Wang, Kundong, et al. "An earthworm-like robotic endoscope system for human intestine: design, analysis, and experiment." Annals of Biomedical Engineering 37.1 (Nov. 2008): 210-221.

Wright, Cornell, et al. "Design and architecture of the unified modular snake robot." Proceedings of the 2102 IEEE International Conference on Robotics and Automation (ICRA). IEEE, pp. 4347-4354, May 2012.

Yanagida, Takaichi, et al. "Development of a peristaltic crawling robot attached to a large intestine endoscope using bellows-type artificial rubber muscles." 2012 IEEE/RSJ International Conference on Intelligent Robots and Systems. pp. 2935-2940. IEEE, Oct. 2012.

* cited by examiner

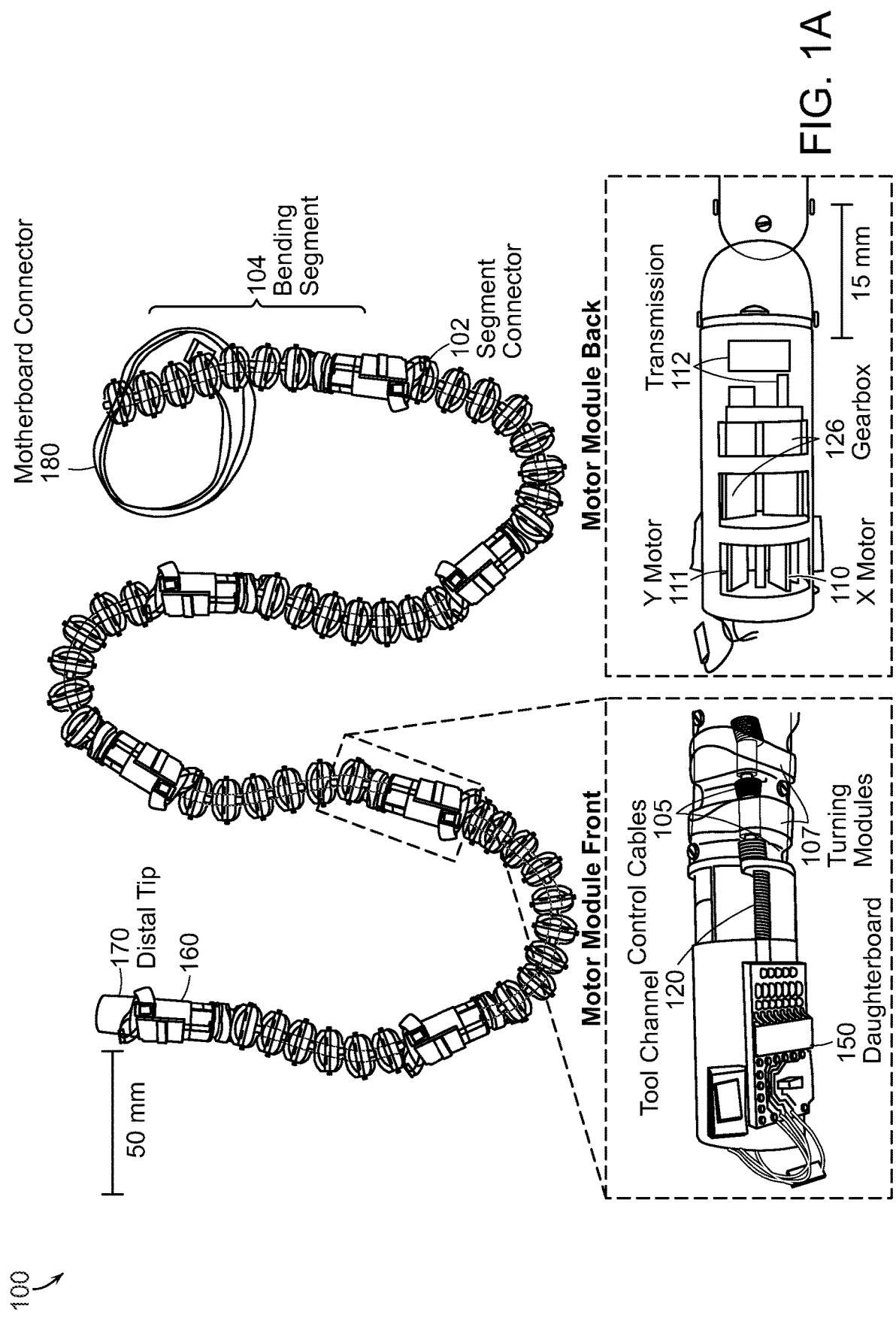

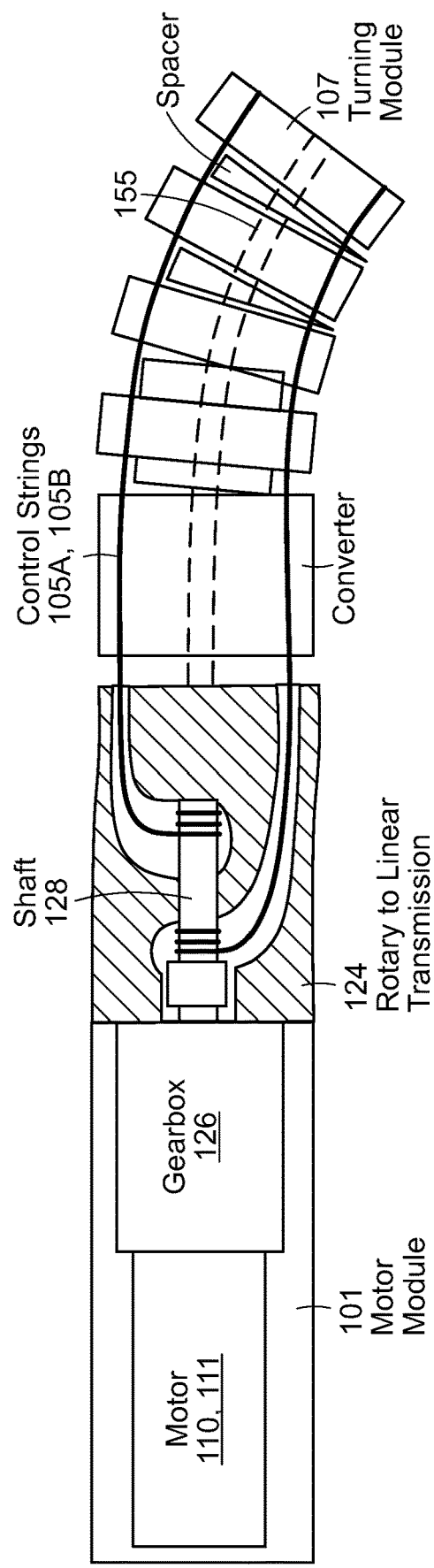
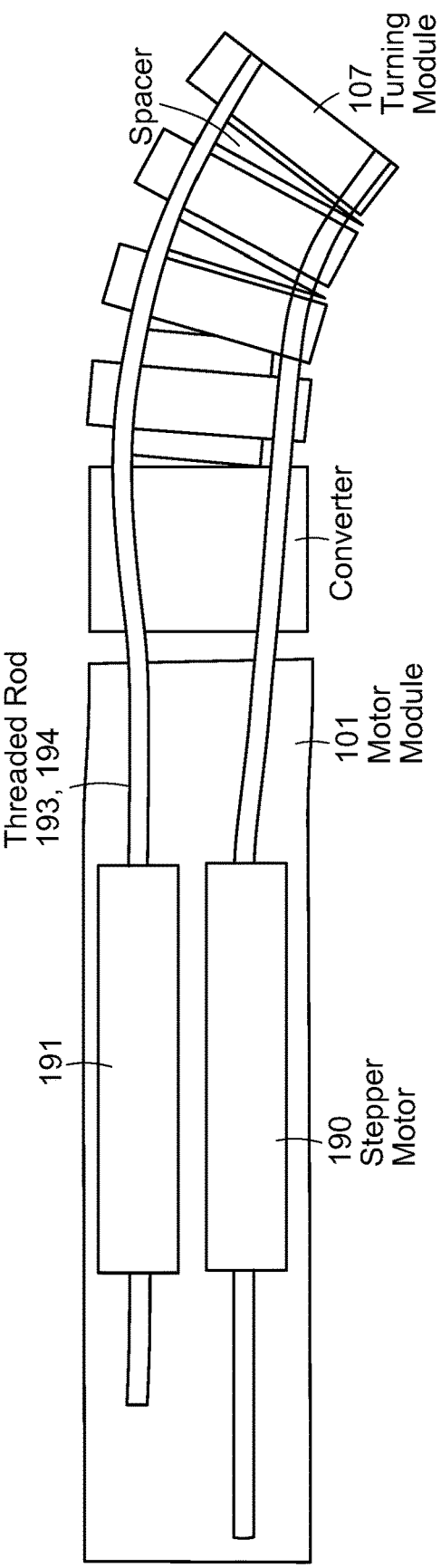
FIG. 1F
FIG. 1G

TABLE I

| Endoscope | Maximum Force (N) Exerted on Wall | | |
|---|---|---|---|
| | A | B | C |
| Conventional | 1.72 ± 0.14 | 1.69 ± 0.24 | 1.06 ± 0.38 |
| Robotic | 0.34 ± 0.08 | 0.20 ± 0.04 | 0.09 ± 0.03 |

TABLE II

| Error | Steady State Tracking Error (degrees) | | |
|---|---|---|---|
| | Uncoiling | Straightening | Follow-The-Leader |
| Mean | 2.78 ± 1.12 | 2.24 ± 1.14 | 3.63 ± 2.00 |
| Maximum | 6.36 ± 2.77 | 4.95 ± 2.64 | 9.85 ± 4.03 |
| Inter-Trial | 1.72 ± 1.12 | 1.47 ± 1.20 | 3.62 ± 2.26 |

TABLE III

| Frame | Steady State Position Range (mm) | | | |
|---|---|---|---|---|
| | Uncoiling | | Follow-The-Leader | |
| | Tip | Body | Tip | Body |
| (i) | 35.3 | 20.7 | 39.3 | 32.3 |
| (ii) | 47.2 | 47.3 | 28.1 | 27.5 |
| (iii) | 68.8 | 47.8 | 38.8 | 59.5 |
| (iv) | 44.7 | 43.7 | 37.1 | 36.7 |

FIG. 11B

Control Overview:

MULTI-LINK MODULAR CONTINUUM ROBOTIC ENDOSCOPE SYSTEM

RELATED APPLICATIONS

This application is a 35 U.S.C. § 371 national stage filing of International Application No. PCT/US2015/028082, filed on Apr. 28, 2015, which claims priority to U.S. Provisional Patent Application No. 61/985,410 filed on Apr. 28, 2014, the entire contents of each of the above applications being incorporated herein by reference.

BACKGROUND OF THE INVENTION

Flexible endoscopy procedures such as colonoscopies are important for diagnostic and therapeutic treatment of colon cancer. Robotic endoscope designs can potentially improve the ability of physicians to position the endoscope, decrease the chance of perforation of the colon, and automate functions so that procedures are easier to complete with a single person. Most commercial endoscopes have a simple bending tip that is driven with Bowden cables down the endoscope body. Automating these systems can be difficult due to the reaction forces and frictional forces generated by tension on the Bowden cables. For these reasons, developing positioning or force output controllers for long cable drive systems and tendon drives is still an ongoing field of research. Several techniques for robotically actuating the bending tip of an endoscope to avoid the use of long control cables have also been developed including using electric motors, shape memory alloys, pneumatics, and other combined techniques.

When a colonoscopy is conducted, it is sometimes difficult to maneuver the endoscope to the end of the colon at the cecum due to the shape of the colon, resulting in incomplete colonoscopies. Some methods that could help improve this process include the use of a crawling system or a double-balloon actuation system to move the endoscope down the colon. These strategies require actively grabbing the walls of the colon and could potentially cause abrasion. Snake-like robot designs have also been considered for this application. While snake-like robotic endoscopes use rigid motorized joints, continuum bending robots have the advantage that they can complete relatively large 180 degree radius bends with a single actuator without producing many discrete corners. For the same number of actuators, a continuum design can also be longer allowing the whole length of the endoscope to be populated with bending segments and not just the tip.

Some continuum endoscope designs have multiple bending points along the length that are driven by several sets of Bowden cables with actuators located at the end. Because of the large number of cables in multi-bend designs, the endoscope becomes thicker the further away from the tip. Follow-the-leader mechanical designs use a single set of cables to create several bends along the length as the endoscope is advanced. These designs can be used to avoid colon walls thereby minimizing abrasion. However, these multi-bend and follow-the-leader designs cannot readily increase the number of bending segments and require complex drive systems at the proximal end.

SUMMARY OF THE INVENTION

The present application relates to a modular continuum robot with multiple bending segments, each containing its own actuation motors. Because of the modular nature of the system wherein the actuation cables are enclosed in each segment, the system scales well lengthwise and does not become thicker when more bending segments are added. By increasing the degrees of freedom of the endoscope, it is possible to move the endoscope in many different ways that cannot be achieved with single bending tip endoscopes. This freedom results in the ability of a physician to easily view different angles inside the colon, thereby minimizing missed detection of abnormalities.

Preferred embodiments use a robot architecture with multiple modular bending segments that communicate with each other and are independently controlled to produce a long hyper-redundant robotic endoscope. Kinematic models can be used to visualize and program trajectories for the robot when the endoscope is inside the patient, away from the view of the physician.

Preferred embodiments utilize a central controller that is connected to segment controllers associated with each segment. Each of the plurality of segments can include a plurality of at least three modules where each module can be oriented along a different axis than adjoining modules. A module in each segment can include a motor connected to each module in the segment to control the angular displacement of each module within the segment. The modules can be aligned along a single common axis, or they can be oriented along a selected curved path at a selected radius of curvature. Each segment can be controlled to have separate or identical radius. Each motor can be collocated with the segment controller in the same or separate module.

The system thus controls coordinated bending motions between the segments to help move the endoscope along convoluted paths. This includes an uncoiling motion used for inserting the robot into the body and obtaining lateral scans of the colon walls as well as a follow-the-leader motion that traverses a path emulating the turns in a colon. The modular robotic endoscope can exert less force on the walls of the colon emulation path than conventional endoscopes.

BRIEF DESCRIPTION OF THE DRAWINGS

FIGS. 1A-1D illustrate several views of modular multi-segment continuum robotic endoscopes without the outer sheaths according to various embodiments.

FIG. 1F illustrates an individual segment of a continuum robotic endoscope according to various embodiments.

FIG. 1G illustrates an individual segment of a continuum robotic endoscope according to various embodiments.

FIG. 11B illustrates the bending angles for each bending segment during the motion shown in FIG. 11A.

DETAILED DESCRIPTION OF THE DRAWINGS

For robotic endoscope applications, there are many possible desirable motions that can be helpful during procedures. Among these motions are a follow-the-leader motion for avoiding colon walls, an uncoiling motion for inserting the endoscope into the body, a linear scanning motion, and a rotary scanning motion for looking at surface features. Each of these motions has a different set of constraints that can be solved to determine the desired sequence of waypoint commands to achieve a given trajectory. In addition, kinematic modeling and simulation are useful for path planning, robot control, as well as visualization of the robot when it is out of view during a procedure.

Figure 1B:
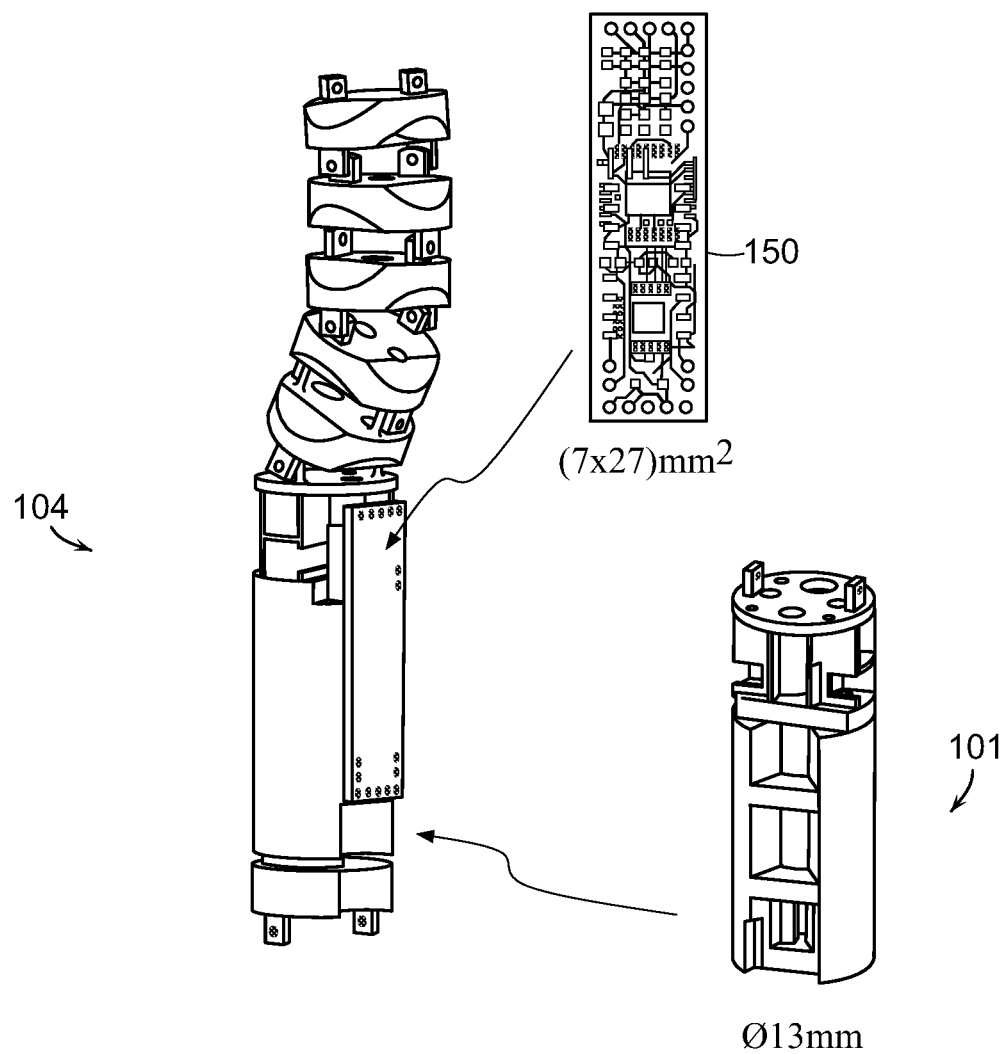
Figure 1C:
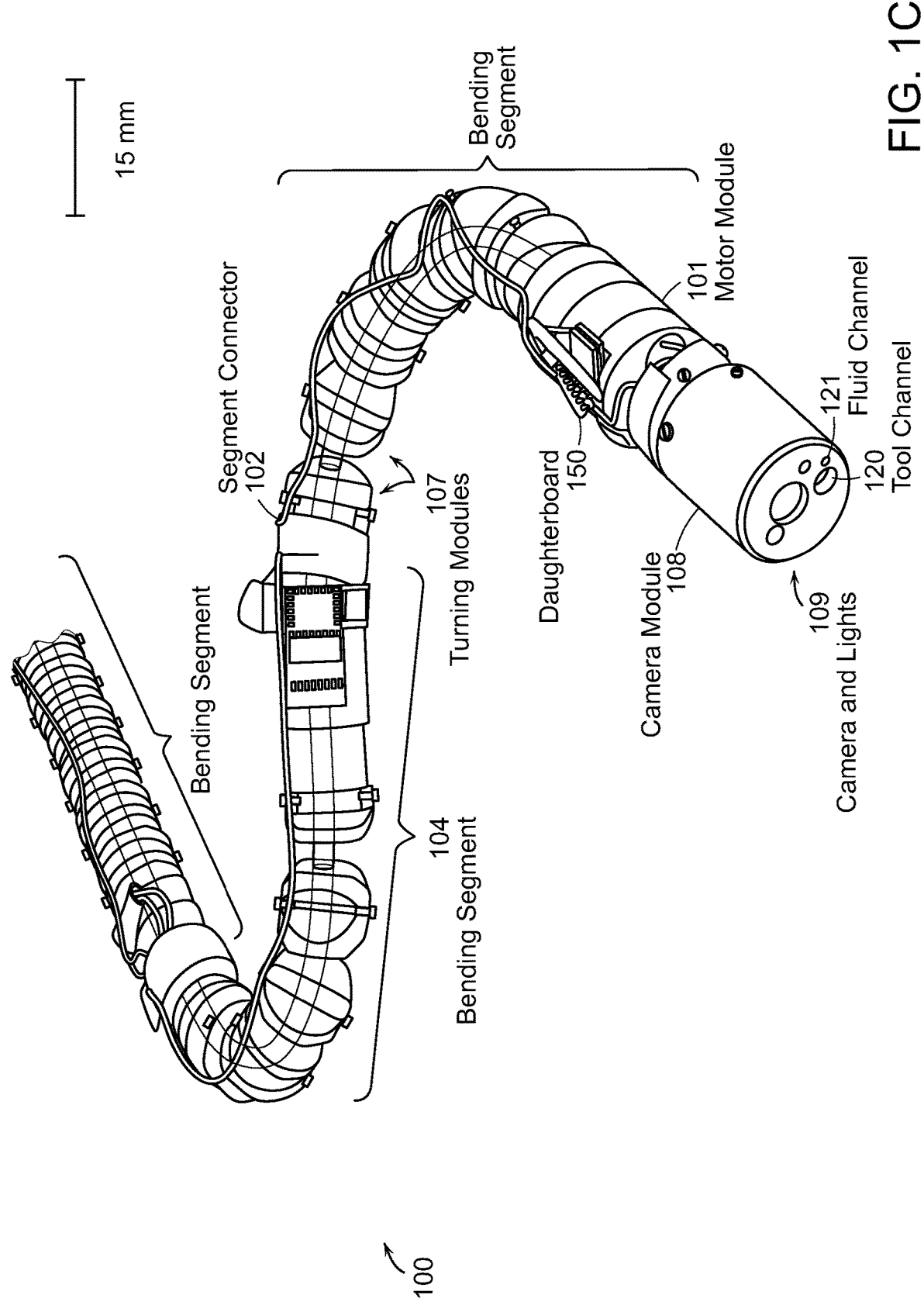

The overall robotic endo scope design can be broken down into several repeated segments as shown in FIGS. 1A and 1C. The mechanical components, electronics, software and communications architecture are modular so that the endoscope can be lengthened by plugging in additional segments, each containing its own daughterboard, motors and turning modules.

Shown in FIG. 1A is a modular endoscope system 100 according to various embodiments further illustrating the front and back of a motor module. The endoscope can have an outer sheath 160 (partially shown) that extends over the entire length, from the distal end 170 to the proximal end 180, to seal the endoscope body in a fluid tight cover. In this embodiment, seven bending segments 104 are shown to create an overall system length of 0.91 m. The system 100 is easily extended by plugging in additional bending segments 104. Each modular bending segment 104 contains an electronics daughterboard 150 and motors 110, 111 that pull control cables 105 in order to turn each segment 104. Further details regarding a programmable computer-controlled modular endoscope system are described in International Application No. PCT/US2011/049167, filed Aug. 25, 2011, the entire contents of this application being incorporated herein by reference.

A smaller embodiment of the present disclosure is depicted in FIG. 1B. The outer diameter of the pictured endoscope motor module 101 is 13 mm as compared to the 15 mm diameter of the module shown in FIG. 1A. In this embodiment, the daughterboard, or segment controller, 150 has dimensions of 7×27 mm. The decrease in size will increase patient comfort during a procedure.

A closer view of an endoscope according to various embodiments is depicted in FIG. 1C. The endoscope 100 comprises a series of bending segments 104 that are linked by segment connectors 102. Each bending segment 104 may contain a motor module 101, a camera module 108, and turning modules 107. A fluid channel 121 and/or a tool channel 120 may pass through the interior of the bending segments 104 and through the segment connector 102. Each bending segment 104 may be controlled by a respective daughterboard 150.

Each continuum turning module 107 houses monofilament cables 105 that turn the assembly in $\varphi_x$ and $\varphi_y$ rotations. The turning modules 107 are constructed through a stereolithography process using Accura SI-60 resin. These modules are connected to each other on joints that allow for $\varphi_x$ and $\varphi_y$ rotations but not twisting motions. Through the center of this assembly is a long, 4 mm diameter plastic-coated spring 123 that serves as the tool channel 120, which can be used to pass biopsy tools through the endoscope and to provide a small restoring force.

The turning modules 107 are then connected to the motor module 101 which contain two 6 mm diameter motors 110, 111 geared at a ratio of 1:136 and connected to rotary-to-linear transmissions 124. Unlike previous designs with lower gear ratios, the motors in this design produce higher forces, are not back drivable, and can be treated as angular displacement output devices up to the stall force. Each motor 110, 111 controls one turning axis; rotating the motor shaft 128 in one direction tightens one control cable 105A which then rotates the continuum bending section 104 in one direction while rotating the motor 110, 111 in the opposing direction rotates the bending section 104 in the opposite direction. The complex motor module 101 design with the built in transmission 124 is manufactured using stereolithography and is 15 mm in diameter by 35 mm in length. Connectors 102 are placed at the end of the module for interfacing the tool passages 120 as well as power and communications wires.

The continuum bending sections 104 and motor modules 101 are repeated to form a long hyper-redundant robot. Each 130 mm long bending segment can bend by 180 degrees to the left, right, upward and downward. This robot can then be covered with a polymer (e.g. black polyurethane) outer coating 160 to protect it from external contamination and water during a procedure. The distal tip of the robotic endoscope houses a camera module 108 and lighting system 109. The proximal end of the robot is connected to a handle through which power and communications signals are routed.

Figure 1D:
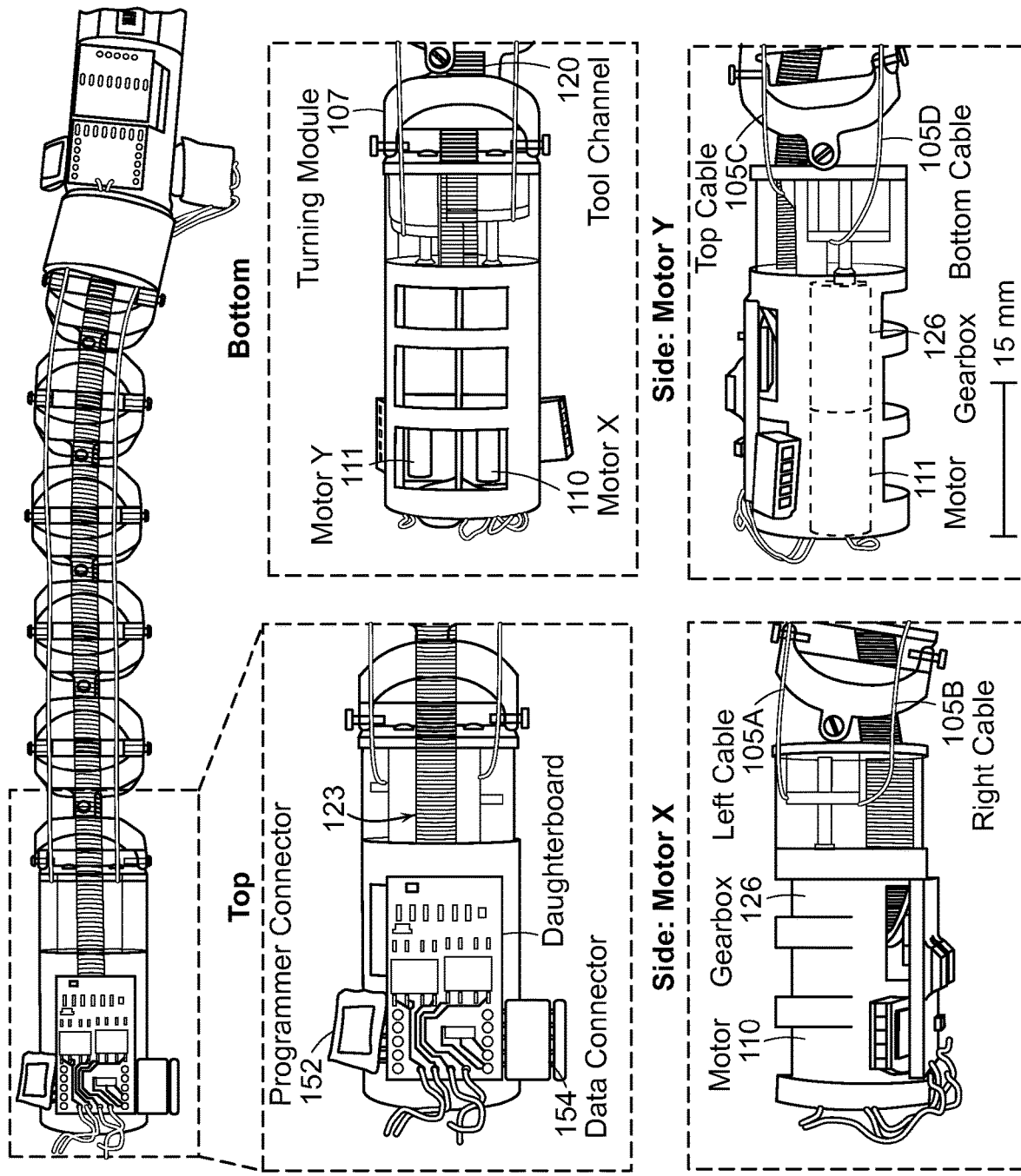

FIG. 1D shows multiple views of a single bending segment 104 according to the present disclosure. The top view of the bending segment 104 illustrates one potential placement of a daughterboard 150, programmer connector 152, and data connector 154. These connectors facilitate communication between bending segments and between the bending segment and programmer. The bottom view of the bending segment 104 illustrates one potential placement of Motor X 110 and Motor Y 111. Each motor individually controls turning motions along its own axis. Also shown are exemplary turning modules 107 and a tool channel 120. Side views of the bending segment 104 show the motor 110, 111, gearbox 126, and cables 105A-D corresponding to each direction.

Figure 1E:
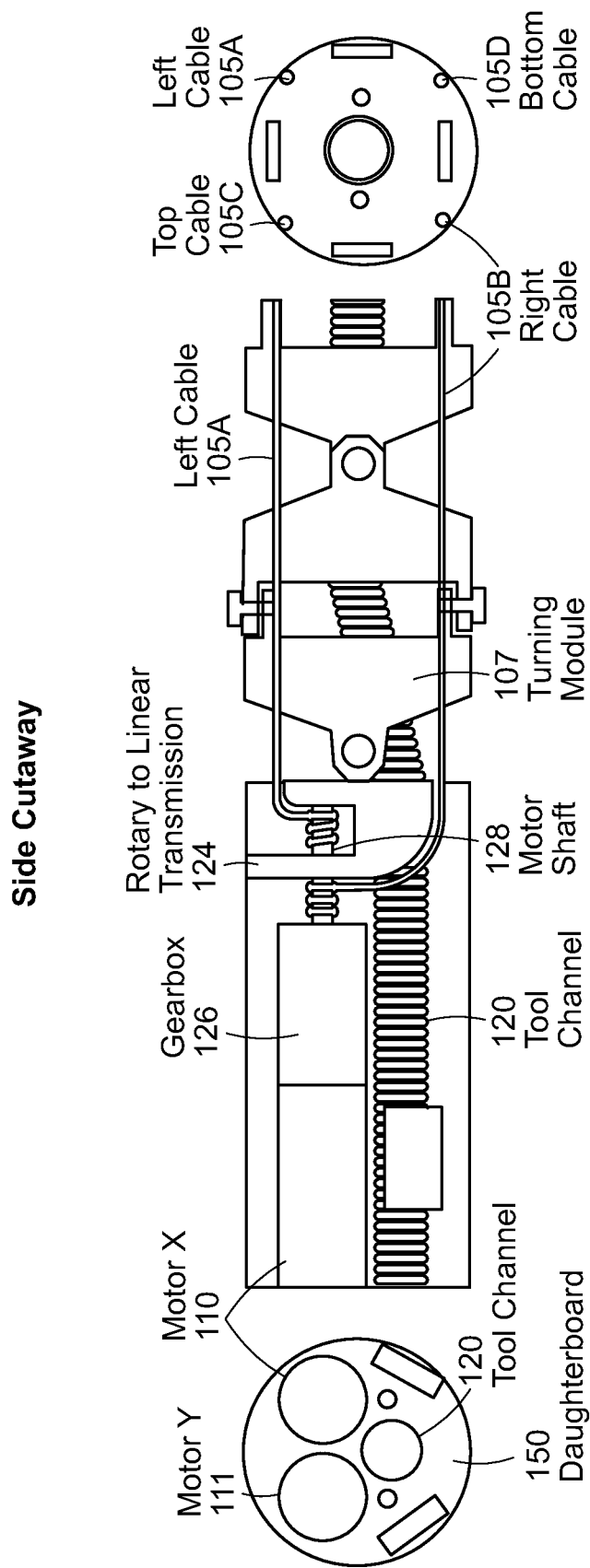
FIG. 1E illustrates a side cutaway of a modular multi-segment continuum robotic endoscope according to various embodiments.

FIG. 1E illustrates side cutaway and end views of a bending segment 104 according to various embodiments. Motor X 110 and Motor Y 111 drive the rotary-to-linear transmission 124 through the gearbox 126. The drive cables 105A, 105B are wrapped around the motor shaft 128; rotation of the shaft 128 in one direction pulls, for example, the right cable 105B while releasing the left cable 105A and rotation of the shaft in the opposite direction pulls the left cable 105A while releasing the right cable 105B.

FIG. 1F illustrates a preferred embodiment of a motor module 101 in cross-section. As illustrated in FIG. 1F, the motor module can comprise a motor 110, 111 coupled to a gear assembly 126 that rotates a shaft 128 that is connected at a distal end to a first control wire 105A and at a proximal end to a second control wire 105B (or the opposite ends of a single wire). By using a rotary to linear transmission 124, a single motor can control movement in opposite directions. A force sensor 155, such as a strain gauge, can be incorporated into the turning module 107. Position sensors and/or gyroscopes can also be used.

FIG. 1G illustrates an alternative embodiment that can produce higher forces by using rotational stepper motors 190, 191. Each of the cables 105 of previous embodiments can be replaced with flexible threaded rods 193, 194 that can be pushed or pulled by a rotational stepper motor 190, 191. Because the threaded rods 193, 194 can be pushed and pulled, two motors 190, 191 can be combined to create a larger bending force for each segment.

Figure 2:
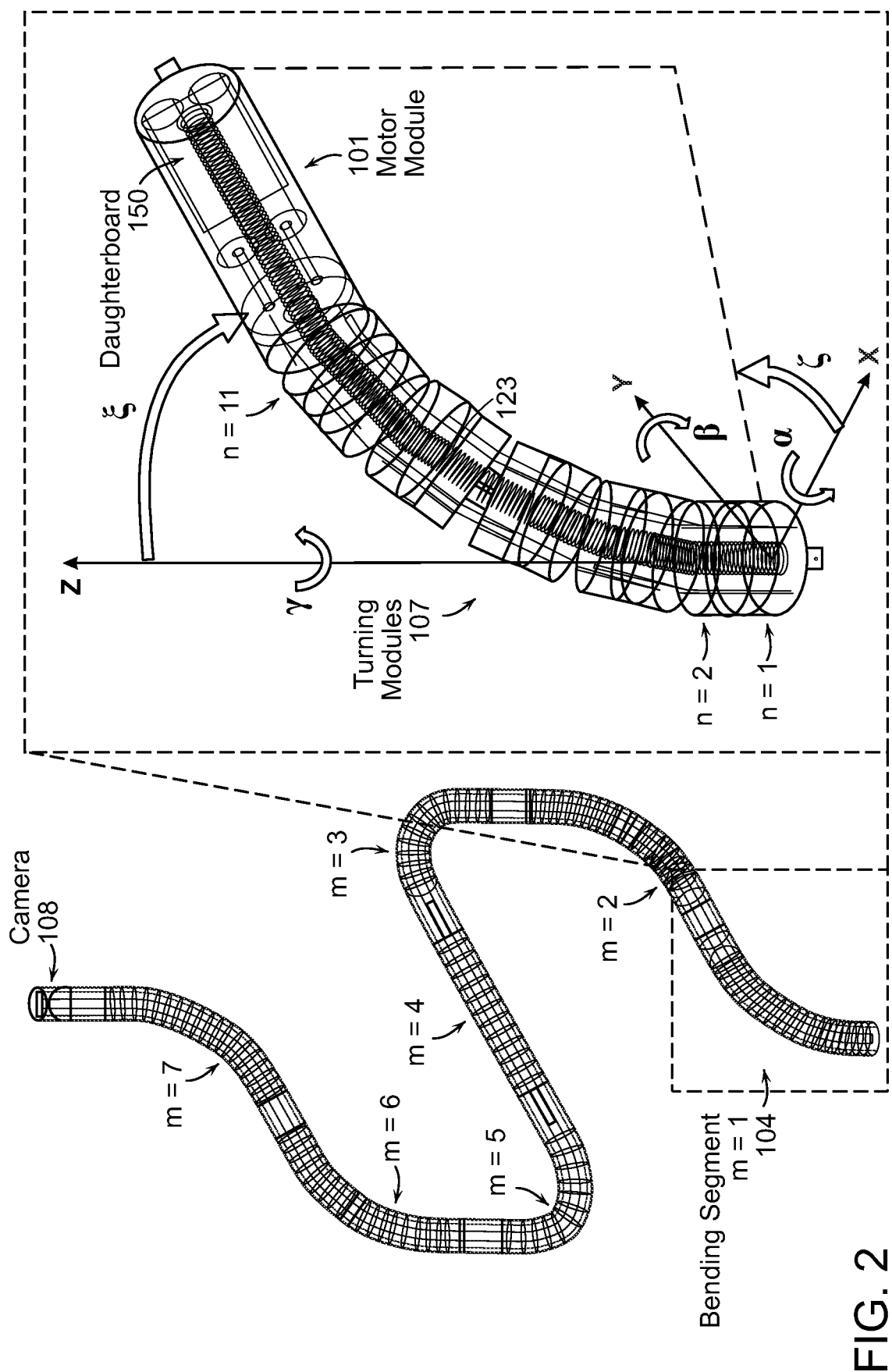
FIG. 2 illustrates a simulation of a robotic endoscope according to various embodiments with M=7 separate bending sections where each bending section has N=11 turning modules.

The kinematic model for a twist-restricted continuum robot differs from the model for a non twist-restricted system. In order to simulate and plan paths for the robotic endoscope, the three dimensional orientation of each turning module in a bending segment can be modeled in Matlab. Each bending segment includes N=11 turning modules where $N_{odd}=6$ and $N_{even}=5$. The overall desired bend angles, as defined by a difference in control cable lengths from the inside of a bend to the outside of a bend, for a single segment m are defined as $\varphi^m_x$ and $\varphi^m_y$. The coordinate system for an exemplary bending segment with yaw, pitch, and roll angles $\alpha$, $\beta$, $\gamma$ is shown in FIG. 2 along with Euler angles $\zeta$ and $\psi_i$. Euler angles can be defined for the system shown in FIG. 2 as, $$\zeta^m = \tan(\varphi^m_y/\varphi^m_x), \quad (1)$$

$$\xi^m = \sqrt{\varphi^{m2}_x + \varphi^{m2}_y}. \quad (2)$$

The angle $\zeta^m$ indicates the relative magnitude between the overall desired bend angles $\varphi_x$ and $\varphi_y$ while $\xi^m$ indicates the magnitude of deflection.

It is important to note that the chord length angles $\varphi^m_x$ and $\varphi^m_y$ (which could be measured by bend sensors or encoders) are not the same as the angles measured by the gyroscope sensors that may be implemented in the robotic endoscope outlined herein. In order to control the full three dimensional rotation of each bending segment, the angles integrated using gyroscope signals also need to be converted to the Euler magnitude angles $\zeta^m$ and $\xi^m$. For a controller that implements x-axis rotations $\alpha^m$ followed by y-axis rotations $\beta^m$, the following equality can be used:

$$R_z(\zeta^m)R_x(\xi^m)R_z(-\zeta^m) = R_z(\gamma^m)R_y(\beta^m)R_x(\alpha^m). \quad (3)$$

Note that for simple two dimensional planar motions, it is possible to approximate $\varphi^m_x \approx \alpha^m$ for odd units and $\varphi^m_y \approx \beta^m$ for even units.

Next, the $X^m_n$, $Y^m_n$ and $Z^m_n$ final location of a series of elements associated with the nth segment can be determined from the initial locations $X_i$, $Y_i$, and $Z_i$ using a rotation matrix $R^m_n$ and a translation matrix $T^m_n$, $$\begin{bmatrix} X^m_n \\ Y^m_n \\ Z^m_n \end{bmatrix} = R^m_n \begin{bmatrix} X_i \\ Y_i \\ Z_i \end{bmatrix} + T^m_n. \quad (4)$$

Since rotational joints are added to prevent twisting motions, each turning module can only rotate in one of the two bending angles and are offset from the control cables by $\zeta^m_n = 45$ degrees. The Euler angles associated with each turning module n, where n is odd, are defined by $\xi^m_n \approx \xi^m \cos(\zeta_m - \zeta^m_n)/N_{odd}$ and, $$R^m_n = R_z(\zeta^m_n)R_x(\xi^m_n)R_z(-\zeta^m_n)R^m_{n-1}. \quad (5)$$

For each turning module n that is even, the rotations are defined by $\xi^m_n \approx \xi^m \sin(\zeta_m - \zeta^m_n)/N_{even}$ and, $$R^m_n = R_z(\zeta^m_n)R_y(\xi^m_n)R_z(-\zeta^m_n)R^m_{n-1}, \quad (6)$$

where the rotations are, $$R_z(\theta) = \begin{bmatrix} \cos(\theta) & \sin(\theta) & 0 \\ -\sin(\theta) & \cos(\theta) & 0 \\ 0 & 0 & 1 \end{bmatrix}, \quad (7-9)$$

$$R_y(\theta) = \begin{bmatrix} \cos(\theta) & 0 & -\sin(\theta) \\ 0 & 1 & 0 \\ \sin(\theta) & 0 & \cos(\theta) \end{bmatrix},$$

$$R_x(\theta) = \begin{bmatrix} 1 & 0 & 0 \\ 0 & \cos(\theta) & \sin(\theta) \\ 0 & -\sin(\theta) & \cos(\theta) \end{bmatrix}.$$

Each simulated element is first rotated by the rotation defined by the previous element $R^m_{n-1}$ and then rotated by $-\zeta^m_n$, bent by $\xi^m_n$ and then rotate back by $-\zeta^m_n$.

The output force normal to the tip of a bending segment can be used to determine the endpoint stiffness of each bending segment of the robot. The output force normal to the tip $F_{ext}$ is $$F_{ext} = \frac{\phi}{L_s} F_{in} e^{-\mu\phi} - K\phi. \quad (10)$$

The pull force of the motor $F_{in}$ is modified by the capstan friction of the bending angle $\varphi$ and the coefficient of friction $\mu$. The internal normal force from string tension is related to the tangential string tension through the radius of curvature of the bent segment $\varphi/L_s$, which is a function of the length of the bending segment $L_s$. Lastly, the endoscope structural stiffness K is included.

From this equation, it is clear that the output force normal to the tip is zero when the bending angle is near zero. Therefore, the endpoint stiffness near low bending angles will be very small. When generating trajectories, configurations that require perfectly straight angles are penalized. Paths with many straight bending segments require an additional straightening algorithm in order to achieve the desired configuration. The kinematic model can be used to describe the location of each element and to coordinate path planning while the tip force model provides insights on the configurations with the lowest endpoint stiffness.

An uncoiling mode can be used to insert the robotic endoscope into the body or move the endoscope for linear scanning. Other robotic endoscope designs commonly use a separate long linear actuator for this purpose or a separate extension or inchworm actuator. In the present system, since each segment is motorized, a coordinated uncoiling motion can be used to insert the endoscope into the body following a set of constraints. For planar motions, $$\sum_m^{M_{uncoil}} \phi_x^m = \phi_{xd} \text{ and } \sum_m^{M_{uncoil}} \phi_y^m = \phi_{yd}. \quad (11)$$

Figure 3:
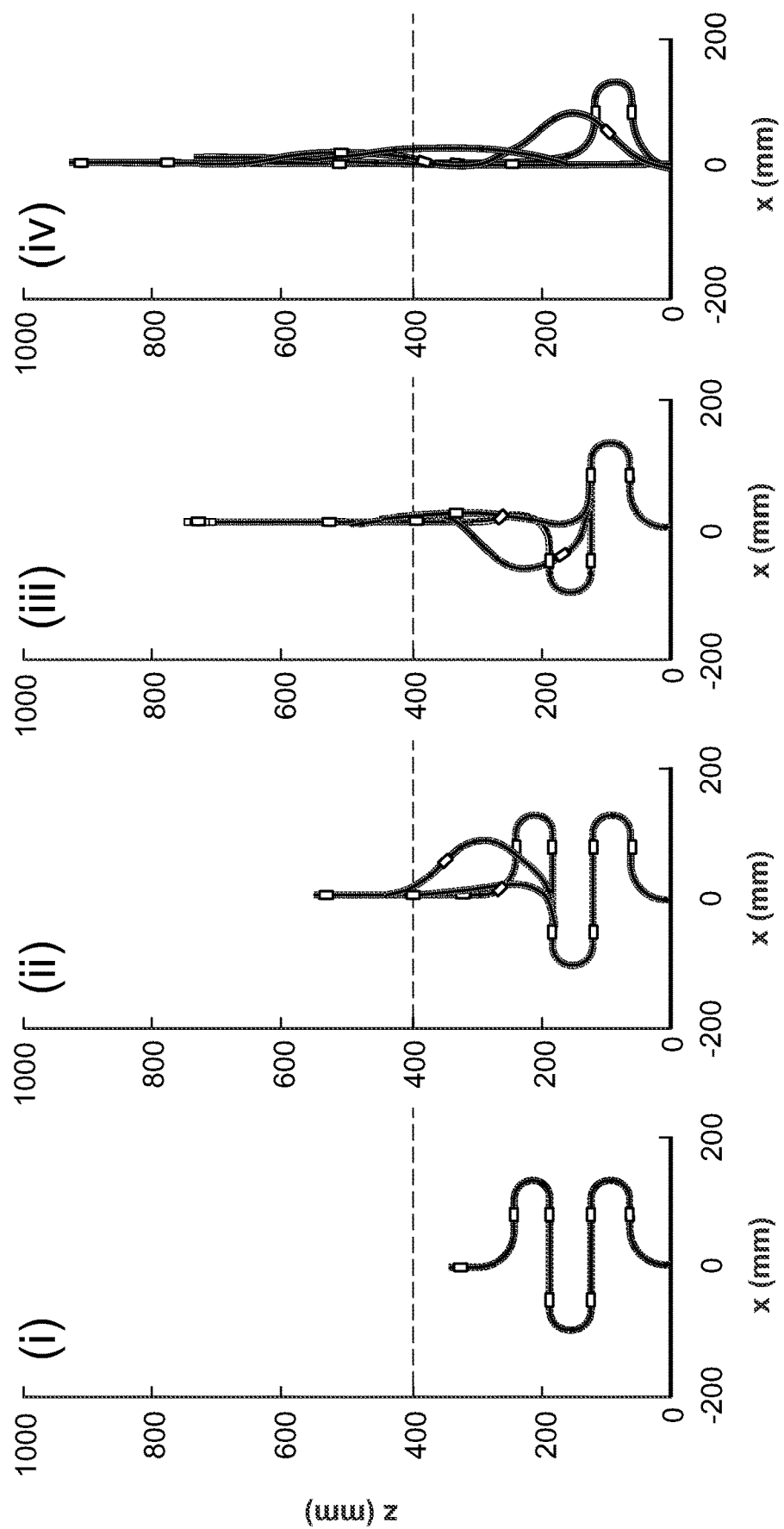
FIG. 3 illustrates a simulation of an uncoiling algorithm for robotic endoscope insertion according to various embodiments for M=7 bending sections.

The sum of all the turning angles for segments within the uncoiling region $M_{uncoil}$ must be equal to the final desired angles $\varphi_{xd}$ and $\varphi_{yd}$. Note that $2\pi n$ multiples of $\varphi_{xd}$ or $\varphi_{yd}$ satisfy configuration constraints but require more complex 3D rotations for uncoiling. In addition, the location of the point within the uncoiling region must be $X^{M_{uncoil}}=X_d$ and $Y^{M_{uncoil}}=Y_d$ and length of the robot outside the uncoil region $L^M - L^{M_{uncoil}} = L_d$. One uncoiling configuration where $\varphi_{xd}=0$, $\varphi_{yd}=0$, $X_d=0$ and $Y_d=0$ is shown in FIG. 3. In FIG. 3, the uncoiling order goes from left to right, and the highlighted area denotes the uncoiling region. By specifying a desired coil length $L_d$, it is possible to generate a set of waypoints for inserting the robotic endoscope into the body without a separate insertion actuator. There are many possible algorithms that can satisfy the constraints. In one embodiment, the algorithm chooses to sequentially uncoil the three segments closest to the exit point. This algorithm uses the fewest number of actuators at any one time to complete the desired task. In order to provide a higher endpoint stiffness, the algorithm avoids bending angles with magnitudes less than 7 degrees.

A follow-the-leader mode can be used to navigate the inside of the colon by following a defined set of bends dictated by the lead bending segment. These bends are then followed by all the subsequent segments when they reach the same position. The locations of these bends may come from x-ray, fluoroscopy, ultrasound and other scans. Modules can include fluoroscopic markers. Alternatively, the bends can be defined as the operators work in real time such that they push the endoscope forward, choose to turn the tip of the endoscope, and have all subsequent bending sections follow the same turns.

The set of bends for the final configuration are defined such that $\Phi_{xd}(mL_s)=\varphi_{xd}^m$ and $\Phi_{yd}(mL_s)=\varphi_{yd}^m$ where each bending segment is $L_s$ long. Ideally, each desired bend is large enough to accommodate two or more bending segments to form a more continuous shape and to reduce deviations from the desired shape. Next, a function is created to interpolate between the desired bends for segments that have entered the body $L_d>(m+1)L_s$:

$$\varphi_x^m(L_d)=f(\Phi_{xd}(L_d-(m+1)L_s)) \quad (12)$$

For regions outside the body, other algorithms like uncoiling can be used or the controller can simply be turned off. An interpolation function f( ) can be used to generate intermediate waypoints. Linear interpolation works best for angles with magnitudes less than 90 degrees but will also work moderately well for larger angles. More complex functions that allow for overshoot to reduce overall positioning error can also be used. In general, bending angles with magnitudes less than 7 degrees are avoided for two or more adjacent bending segments in order to provide a higher endpoint stiffness.

Figure 4:
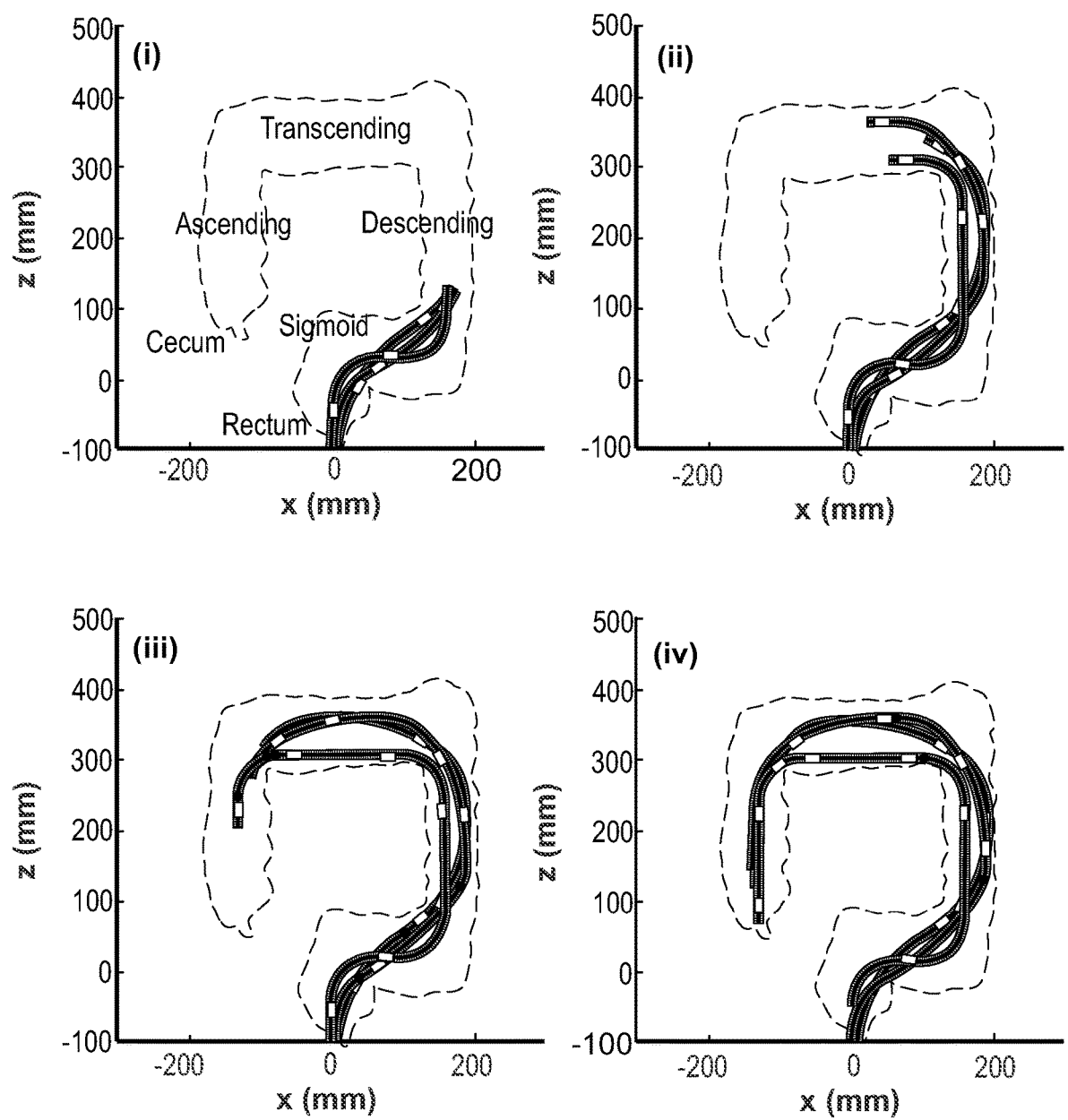
FIG. 4 illustrates a simulation of a follow-the-leader algorithm that shows how the robotic endoscope may be used to traverse a convoluted path according to various embodiments.

A simplified path in FIG. 4 that emulates the turns in the colon (excluding colon pleats and three dimensional bends) shows four 90 degree bends. The simulation uses M=7 bending sections with several different desired lengths $L_d$ shown together on the same plot. The follow-the-leader order goes from left to right and from top to bottom with the shape of a colon highlighted in pink for reference. Different parts of the colon, including the rectum, sigmoid, descending, transverse, ascending, and cecum are labeled. The modular nature of the bends creates conformation errors; here, the maximum deviation from the basic desired path is about 52 mm for a total desired length of $L_d$=910 mm. This path planning paradigm provides higher endpoint stiffness, is fast and easy to compute and works for both previously defined paths as well as paths generated during the procedure. This path planning method also has the benefit of being able to modify any of the bends during the procedure if the path constraints happen to change, such as when the patient moves.

Figure 5A:
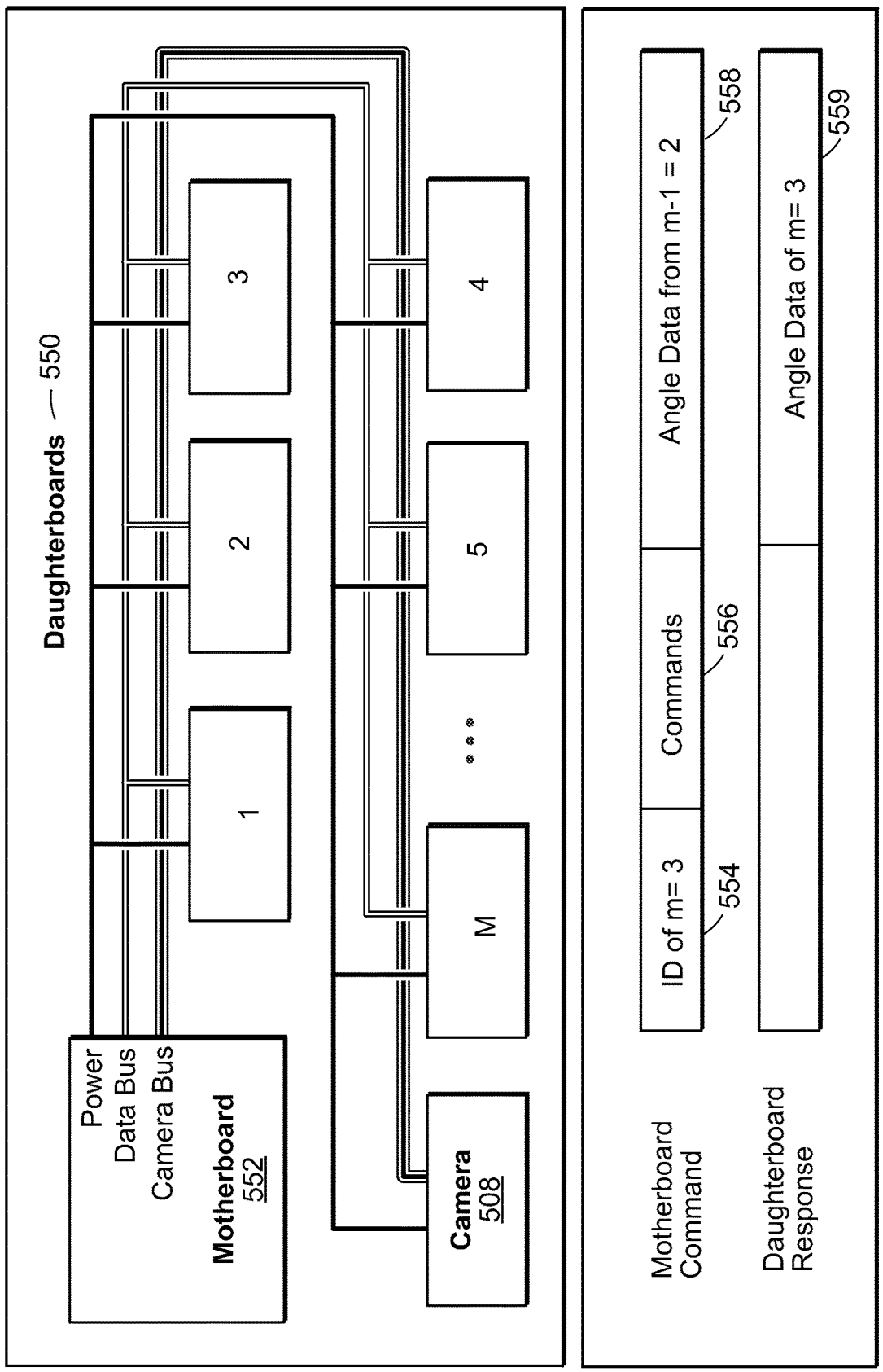
FIGS. 5A-5E illustrate an exemplary computer controlled arrangement with multiple data processor elements to enable communication among the modular boards according to various embodiments.

As shown in FIG. 5A, the electronics architecture is composed of a central controller or motherboard 552 located at the outside of the robot and several daughterboards, or segment controllers, 550, each of which is located on a motor module 101. The motherboard 552 provides power, USB communications with a computer and an Arm Cortex M3 micro controller. The electronics design for the daughterboards 550 are small 10×20 mm or 7×27 mm circuit boards that can include an Arm Cortex M3 micro controller, two H-bridge motor drivers, and an Invensense MPU-6000 MEMS gyroscope and accelerometer, for example.

The motherboard 552 communicates with the daughterboards 550 using a serial peripheral interface with all the daughterboards 552 sharing the same output bus as shown in the top half of FIG. 5A. The motherboard, or central controller, 552 sends commands 556 to each daughterboard 550 separately using unique IDs 554 and each daughterboard 550 responds by reporting 559 angles integrated on the micro controller. To prevent bus contention, the daughterboard 550 outputs only turn on when their unique IDs 554 are called. The bending angle of each section is determined by the difference between the angles calculated on a module m and the module connected to it m−1 as shown in the bottom half of FIG. 5A. Therefore, the motherboard 552 also supplies the angle data 558 from module m−1 to module m. The relative bend angles are then calculated and used for independent closed loop angle control on each segment.

Figure 5B:
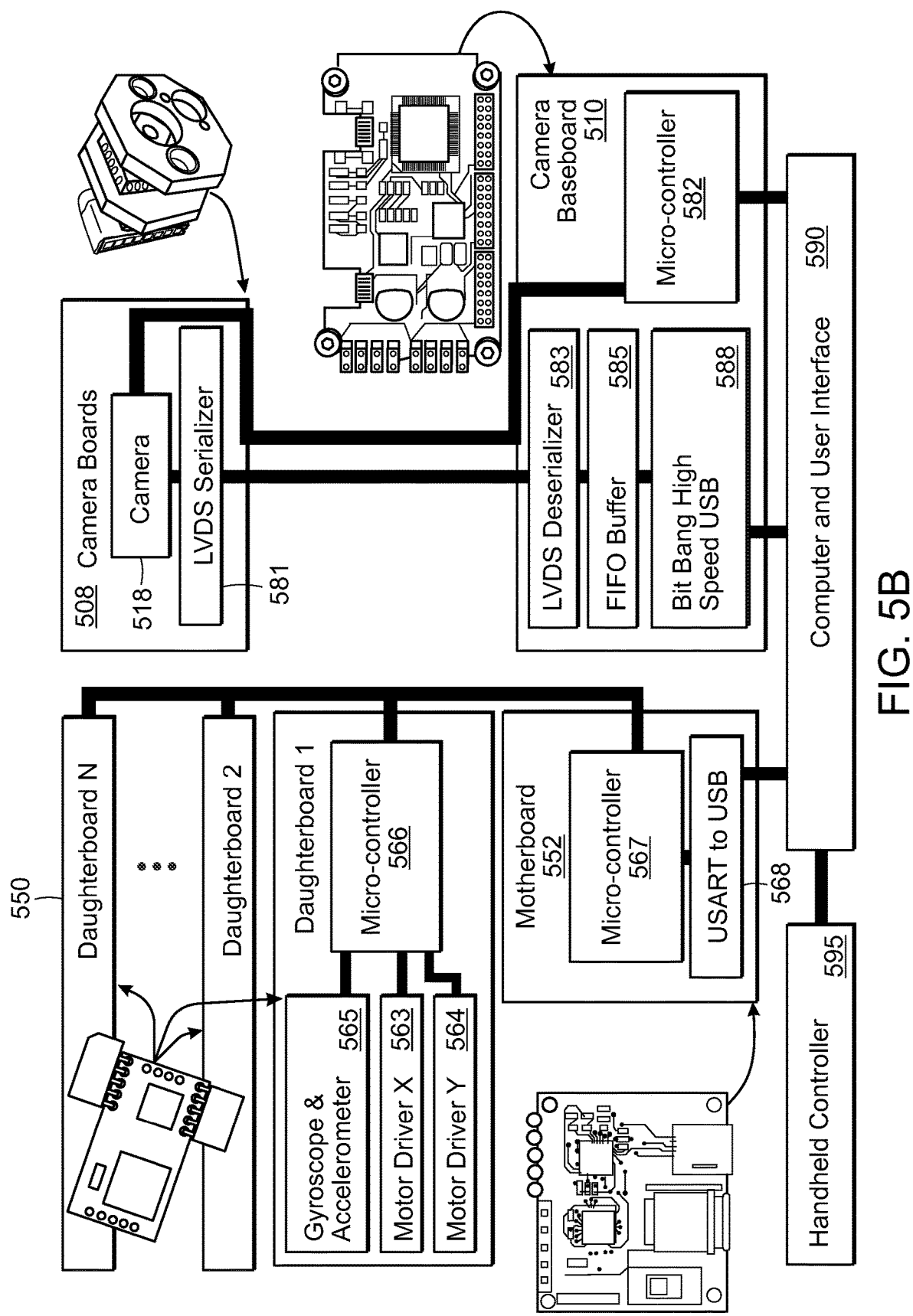

A block diagram of an endoscope system according to the present disclosure is shown in FIG. 5B. Each of the N daughterboards 550 contains a microcontroller 566, gyroscope and accelerometer 565, and motor drivers for the X 563 and Y 564 directions. Each daughterboard 550 is connected to the motherboard 552, which contains a microcontroller 567 and a USART to USB module 568. The USART to USB module 568 connects to the computer and user interface 590, which is in turn connected to the handheld controller 595. The camera boards 508 in each endoscope segment 104 contain a camera 518 and a linear voltage differential signaling (LVDS) serializer 581. The camera 518 connects directly from the camera board 508 to a microcontroller 582 on the camera baseboard 510 while the LVDS serializer 581 connects from the camera board 508 to the LVDS deserializer 583 on the camera baseboard 510. The camera baseboard 510 also contains a FIFO buffer 585 and a bit bang high speed USB 587. The video data are deserialized 583 on the motherboard side, buffered and sent via high speed USB 587 to the computer 590. The computer software and user interface controlling the commands to the motherboard 552 and daughterboards 550 is written in C# or C++. In specific embodiments, the camera 518 used in the system may be a 30 fps VGA format camera (Toshiba TCM8230MD). The raw data may be encoded and decoded across long twisted pair cable using an LVDS serializer 581 and deserializer 583 (SN65LV1224). The decoded data is buffered 585 (IDT72245LB15) and sent through a high speed USB chip 587 to the main computer 590 (FTDI FT2232H). The settings on the camera 518 are adjusted using a microcontroller 582 on the camera baseboard 510. It will be understood by those skilled in the art that the present system disclosure is not limited to these specific elements nor to the given exemplary part numbers.

Figure 5C:
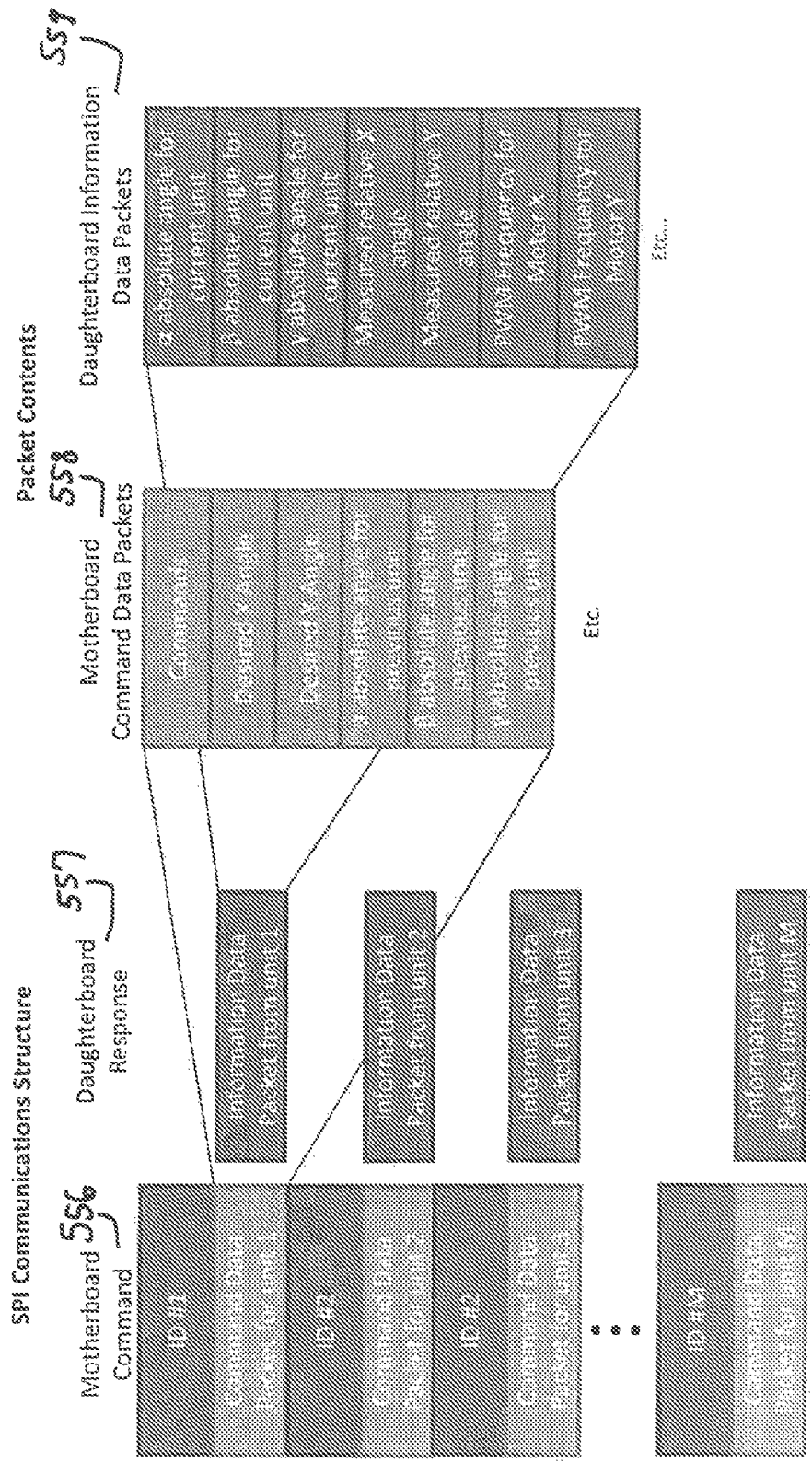

The communications protocol used between the motherboard 552 and the daughterboards 550 is a custom serial peripheral interface (SPI) protocol as shown in FIG. 5C. In this protocol, each daughterboard 550 has a unique ID number 554. When the ID number 554 of the previous unit is called, the daughterboard 550 turns on its output line. When the ID number 554 of the current unit is called, the motherboard sends a set of commands 556 (including desired angles, LED indicator settings, and controller settings) along with the absolute angle data of the previous unit 558. The current unit responds 557 to the motherboard 552 by sending its own absolute angle data, relative angle data, and motor commands executed 559. By subtracting the absolute angle of the previous unit with the absolute angle measured by the current unit, each unit is able to calculate the angle difference and therefore the bend angle of each unit.

Figure 5D:
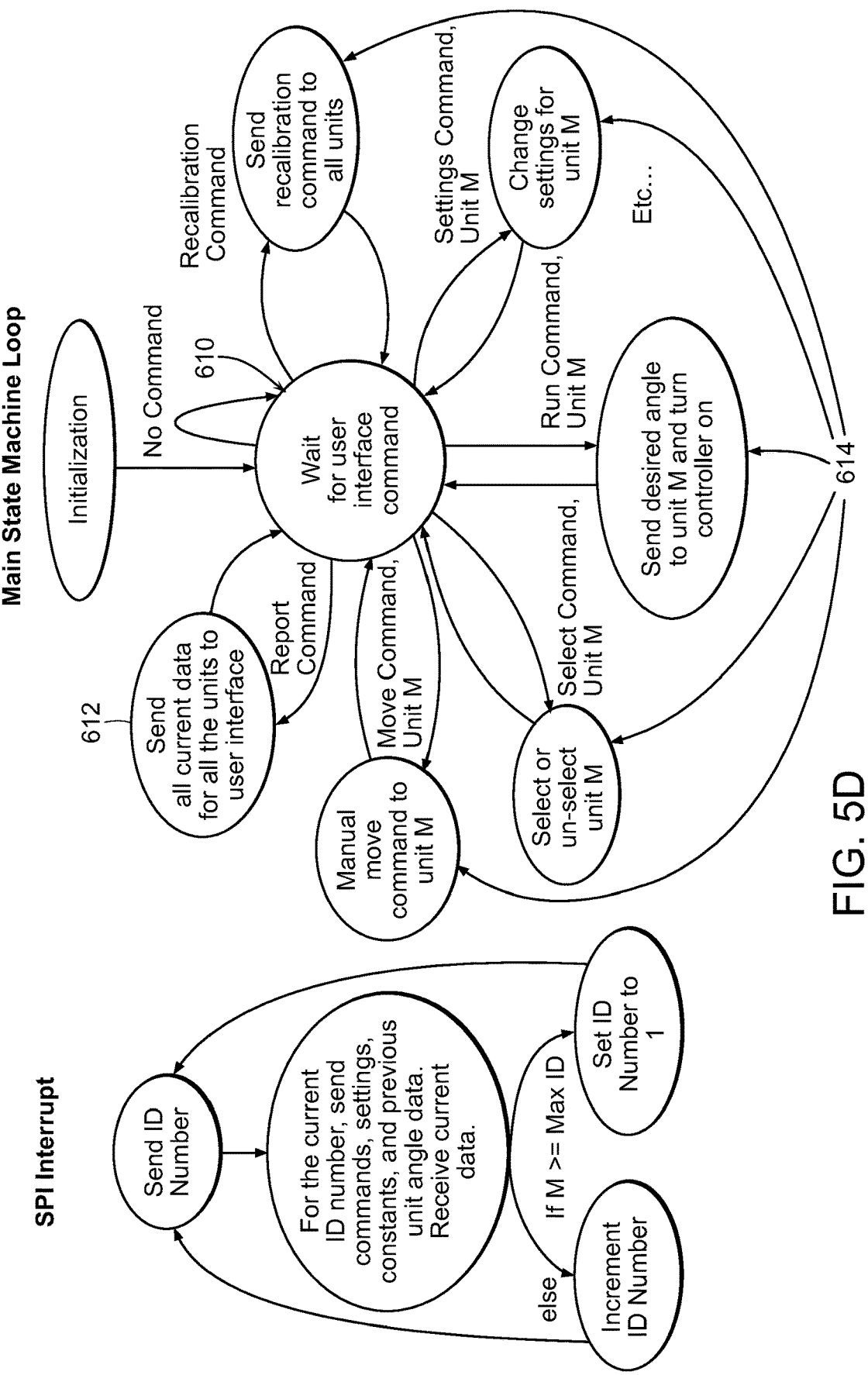
Figure 5E:
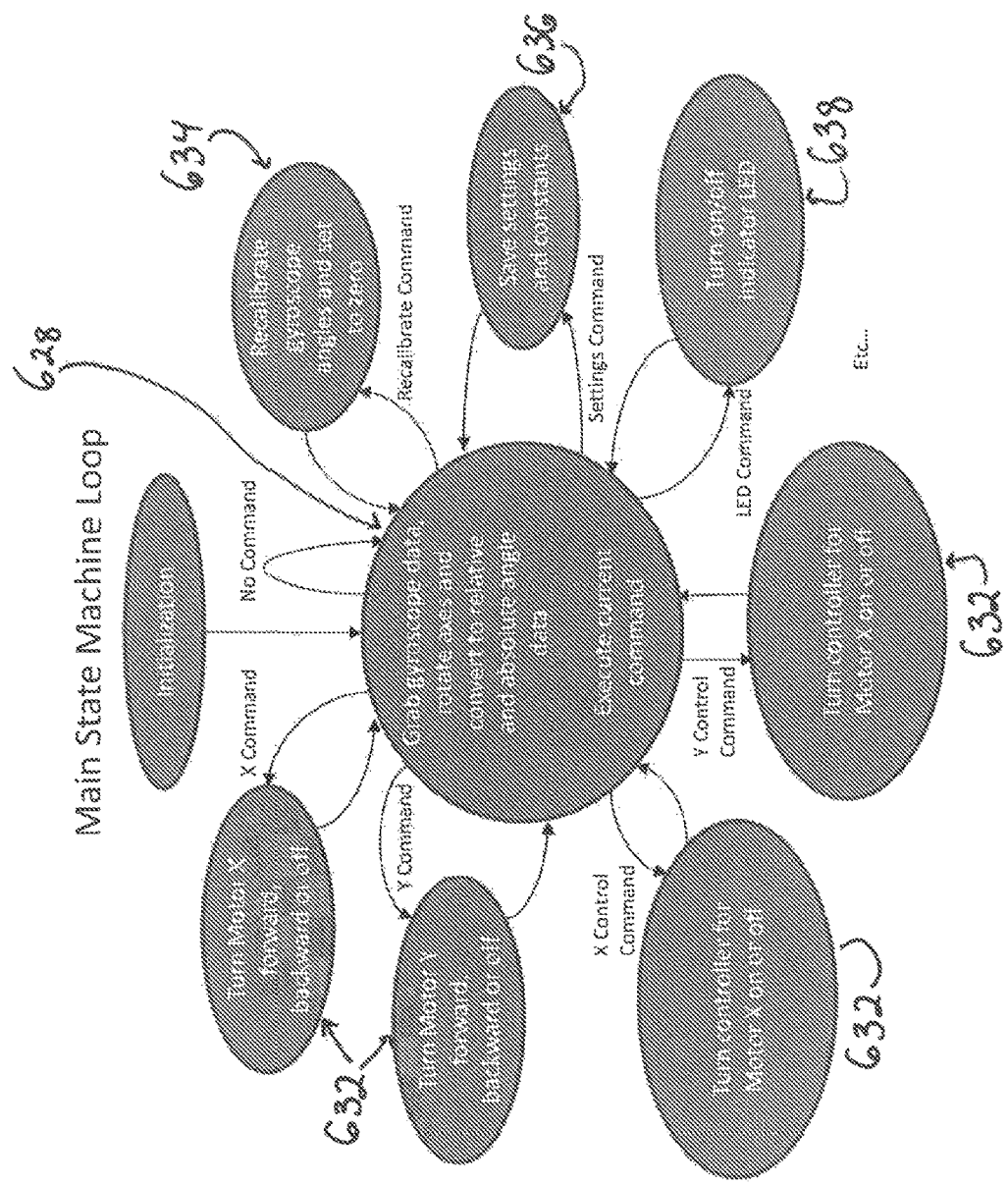
Figure 5E:
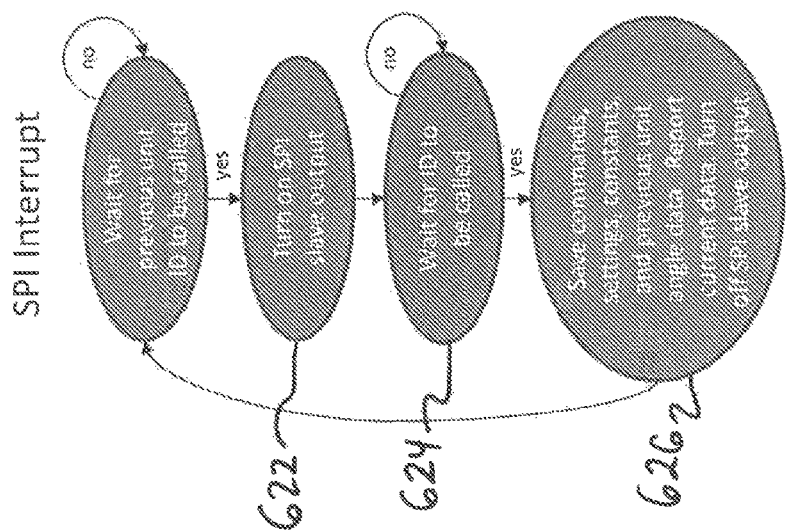

The simplified state machine diagrams of the motherboard, or system controller, and daughterboard, or segment controller, are shown in FIGS. 5D and 5E, respectively. The motherboard waits for commands from the user interface 610 and when a command is received, the motherboard sends the command information 614 to all the daughterboards from unit 1 to unit M where M is the total number of units in sequence. The motherboard is also able to send all the unit data back to the user interface for graphing and visualization 612. The daughterboard state machine turns on its SPI slave output when the previous ID number is called 622. When it receives its own ID number 624, it records the commands from the motherboard and sends all the current data 626. The main loop for the daughterboard (right side of FIG. 5E) constantly grabs the gyroscope data, integrates it, computes the axis rotation and calculates the relative angle 628. If a command is sent, the daughterboard will turn on the controllers to rotate the X or Y motors 632, recalibrate the gyroscope 634, save settings 636 or turn on or off the indicator LED 638. Additional states exist on both boards to allow settings to be updated or the motors to be moved. Higher level multi-unit motions are coordinated by the user interface.

The performance of a single segment as well as the performance of a chain of segments has been analyzed. The paths generated for coordinated motions are implemented and simulation data are compared with measured results.

Figure 6:
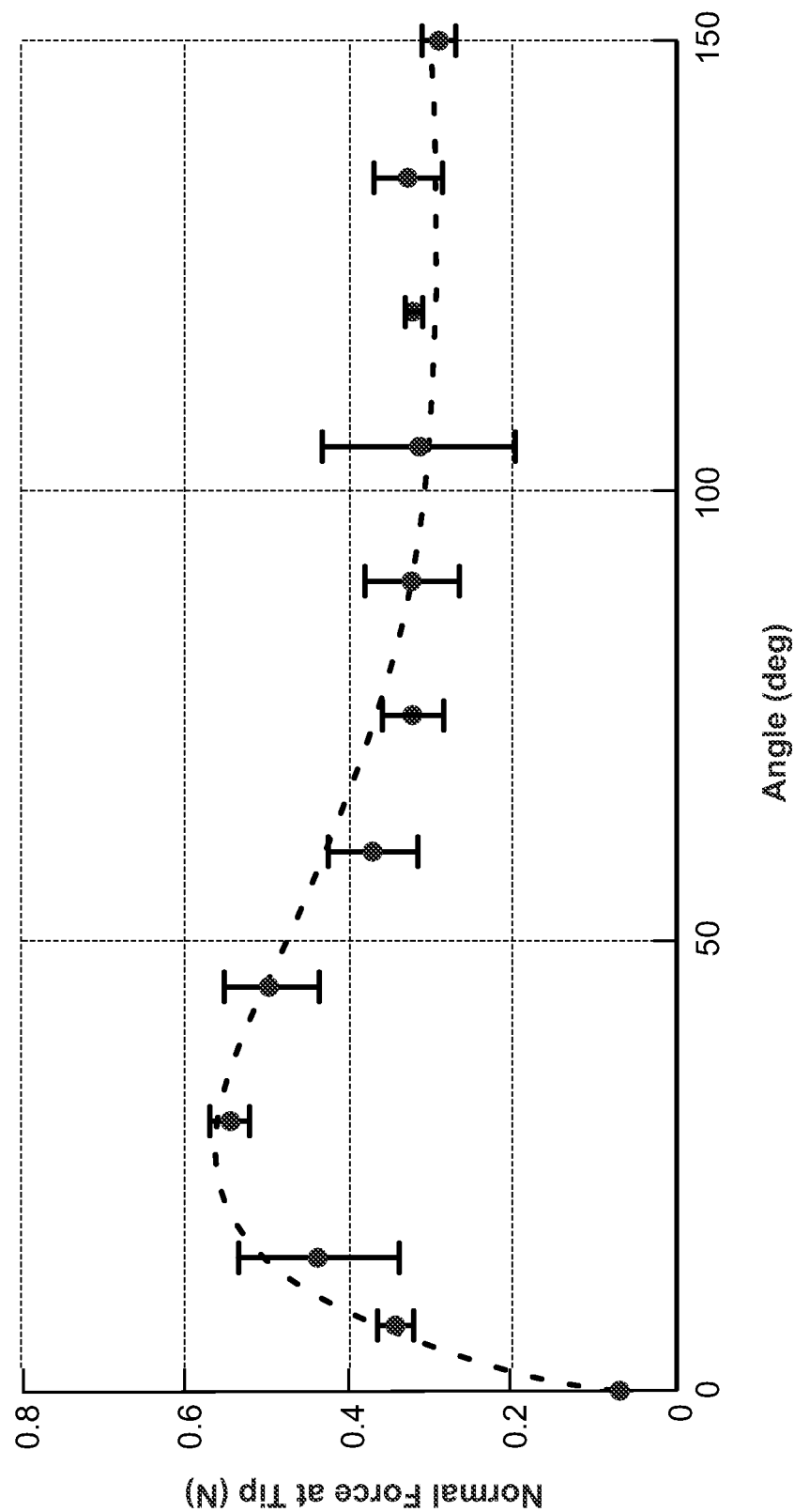
FIG. 6 illustrates normal tip force as a function of bending angle according to various embodiments.

The static output force normal to the tip of a bending segment as a function of bending angle is shown in FIG. 6. The output force is shown for a single bending segment with motor voltage limited to 3 V. The dotted line serves as a guide for the eye. As predicted by Equation 10, when the bending angle is near zero, the normal force output is very small leading to a low endpoint stiffness when the bending segments are straight. The maximum output force and endpoint stiffness occurs near 25 to 30 degrees. Based on this information, paths that utilize angles larger than 7 degrees in magnitude can have better disturbance rejection and can therefore be used as a lower limit for path planning algorithms.

Figure 7:
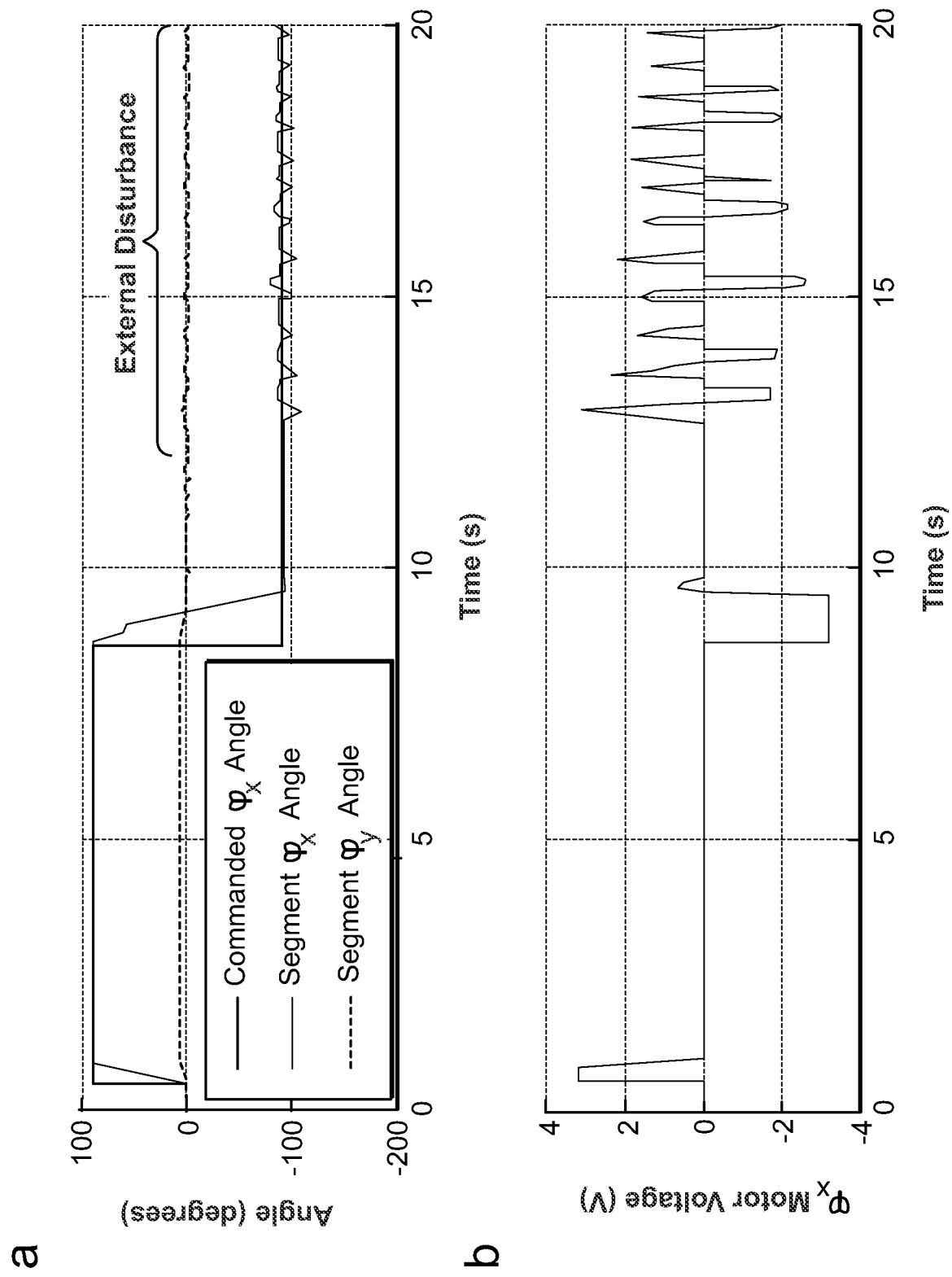
FIGS. 7A and 7B illustrate a closed loop response to a command and voltage output according to various embodiments.

A closed loop controller is generated to control the desired $\varphi_x$ and $\varphi_y$ rotations. The controller takes in proportional and derivative gains, performs dead band compensation, and converts the desired output voltage to a pulse-width modulation (PWM) signal that is sent to the H-bridge motor controller. The closed loop dynamics of one unloaded segment is shown in FIGS. 7A and 7A. In FIG. 7A, the closed loop response to a command in the $\varphi_x$ bending axis is shown along with disturbance rejection capabilities while FIG. 7B shows the voltage output to the $\varphi_y$ motor. The segment is commanded to bend in 90 degrees and then −90 degrees and then the bending segment is tapped to show disturbance rejection. The 3V output-limited slew rate of the module is 250 degrees, and the angle control tolerance is set to 2 degrees. The parasitic rotation in the $\varphi_y$ axis is less than 7%.

Figure 8:
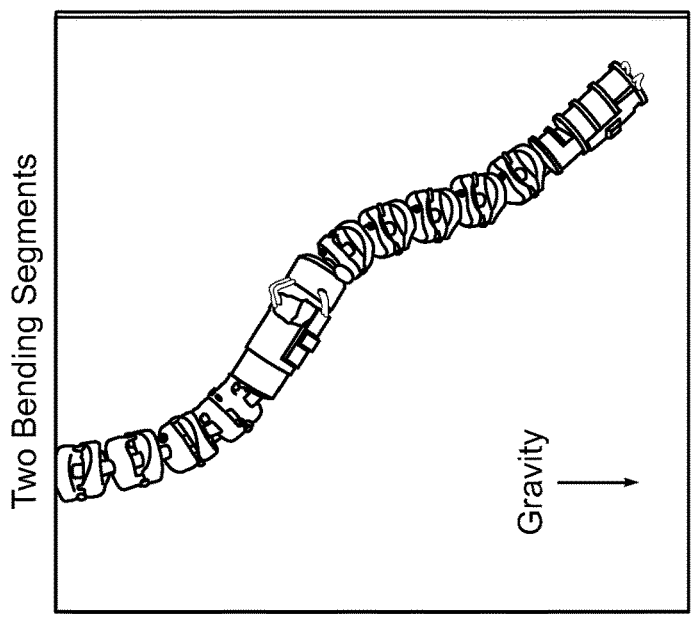
FIG. 8 illustrates an endoscope according to various embodiments attempting to lift its own weight against gravity.
Figure 8:
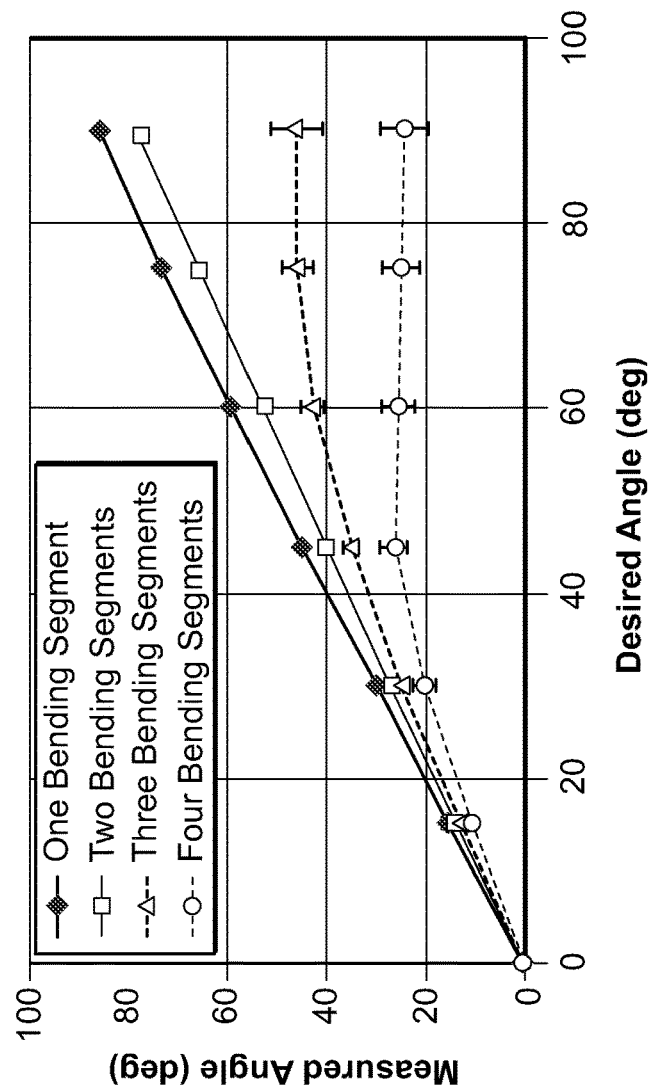

The stiffness of the bending segments can also be modulated in this system. When the bending segment is straight with motors off, the stiffness of the endoscope comes from the spring that is used for the tool channel, the stiffness of the wires, and the stiffness of the rotating joints. This baseline stiffness is between 3.0 and 4.1 mN/degree. When the bending segment is straight with motors on, the stiffness of the endoscope comes from the stiffness of the monofilament cables and the force output of the motors and is between 9.0 and 12.9 mN/degree. The maximum force output normal to the tip of a single bending section at 3 V is approximately 0.6 N. Since each bending segment has a mass of 22 g, each segment is capable of lifting up to 2.7 times its own weight. FIG. 8 shows how gravity effects the ability of the module to rotate to different angles. In this experiment, one base unit hangs freely with gravity pointing down. It is then commanded to different angles with zero to three additional units attached to the end. The panel on the left shows one additional unit attached (a total of two bending segments). Five tests were conducted for each data point. The final measured angle clearly shows that the effect of lifting one additional unit is small. However, the endoscope can only achieve 20 to 30 degrees of rotation with three units of load (total of four bending segments).

The robot used for the coordinated motion measurements is a seven bending segment robot that is 0.91 m long, has a mass of 157 g, and has 14 degrees of freedom (2 degrees of freedom per segment). To analyze coordinated paths, white circular obstacles are used on a metal table that is covered with a thin Teflon sheet to reduce friction. Several large increment waypoints are set in order to reduce the effect of static friction. Due to the mass of the conjoined segments, the robot's bending speed is much slower than that of a single bending segment, and the speed can vary from 35 degrees per second to 200 degrees per second.

Figure 9A:
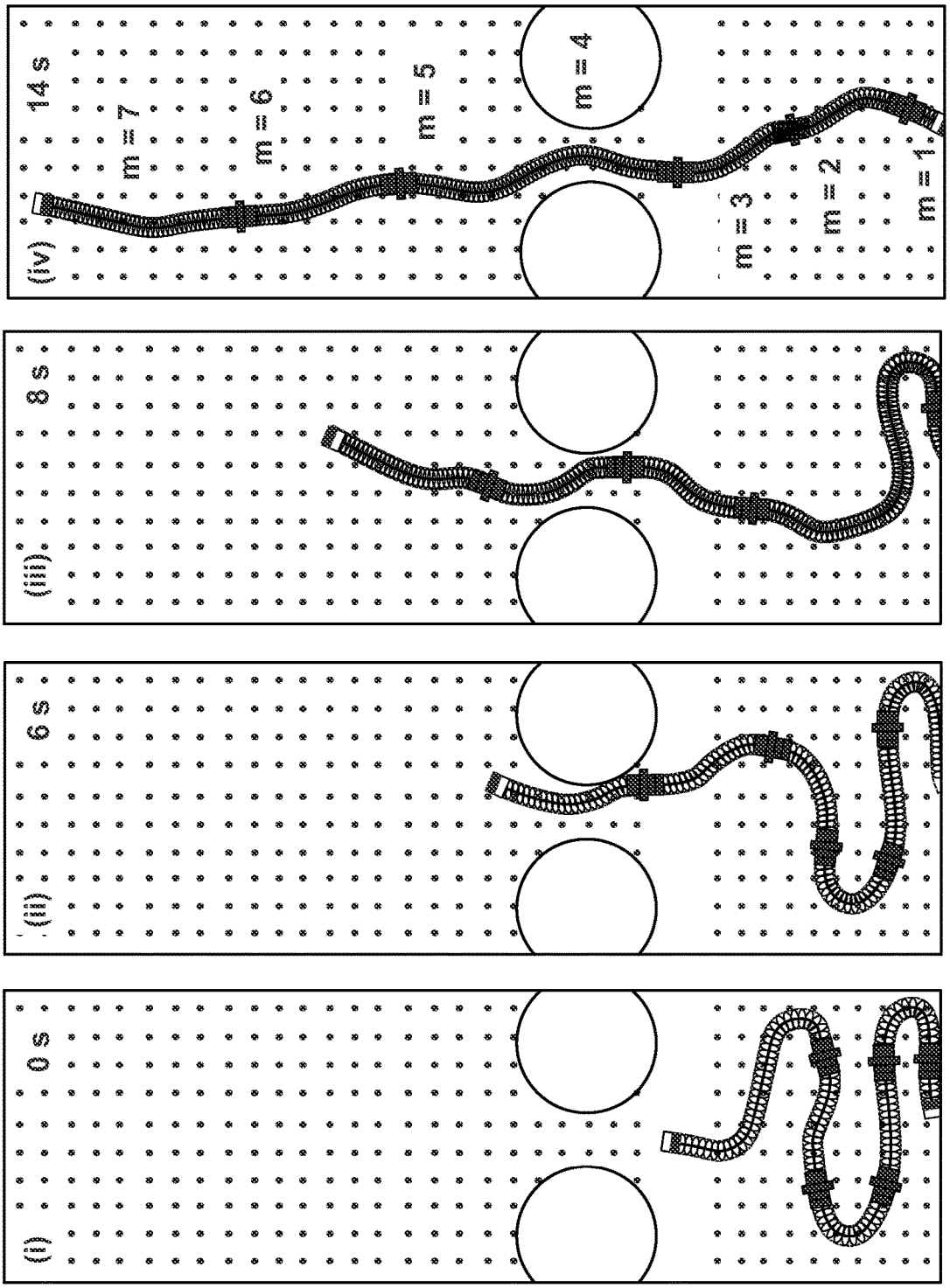
FIGS. 9A and 9B illustrate an endoscope according to various embodiments as it executes an exemplary uncoiling algorithm.
Figure 9B:
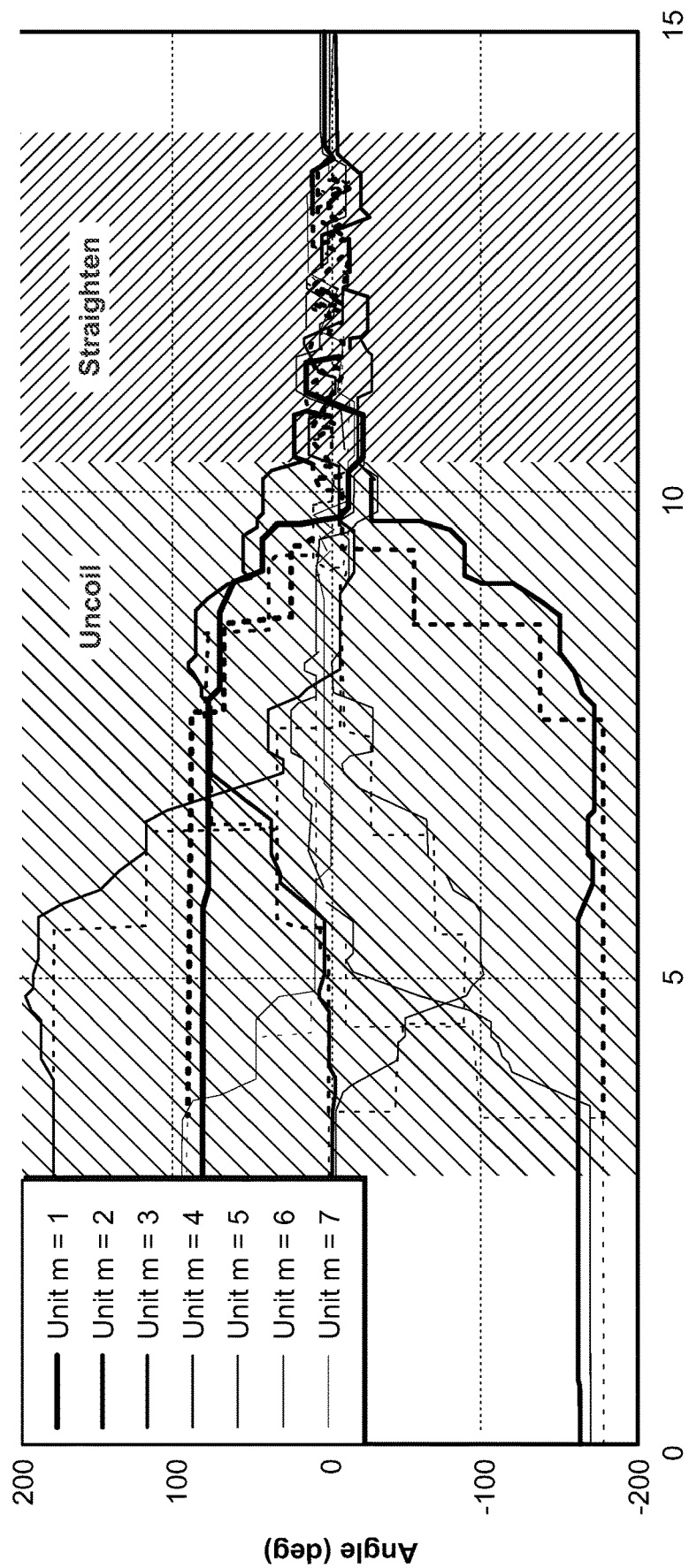

FIG. 9A shows snapshots from the uncoiling path planned earlier in FIG. 3 for insertion into the body without using additional insertion actuators. In FIG. 9B, time-series data of the desired bending angles (dotted lines) and measured closed loop bending angles (solid lines) are given for each of the seven bending segments for the uncoiling and straightening modes. As shown in FIG. 9B, the desired angles are generally maintained by the controllers on each module. However, external friction, play in the modules, and the overall mass of the system does prevent the robot from achieving all the desired angles perfectly with errors that can be as large as 30 to 40 degrees for units near the proximal end. Despite missing the desired angle at some waypoints, the robot eventually catches up to the desired angle thereby achieving the desired configuration. In general, the robot does release from the coiled state and the angular errors are less than 10 degrees. After the uncoiling state, the robot is not perfectly straight due to low endpoint stiffness for angles near zero degrees. Therefore, a straightening algorithm is added which moves the bending segments back and forth slightly to overcome friction.

Figure 10A:
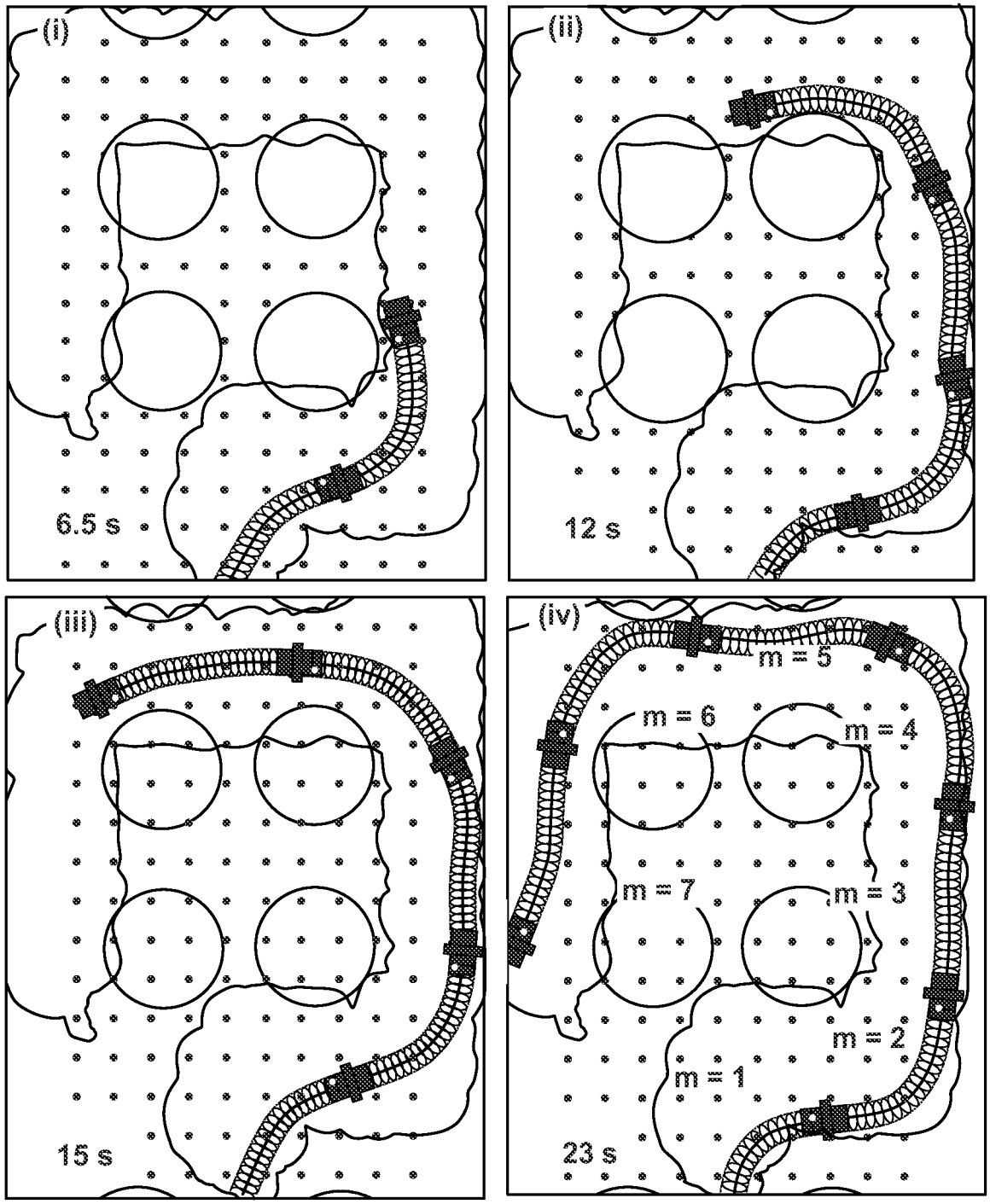
FIGS. 10A and 10B illustrate an endoscope according to various embodiments as it executes a follow-the-leader algorithm.
Figure 10B:
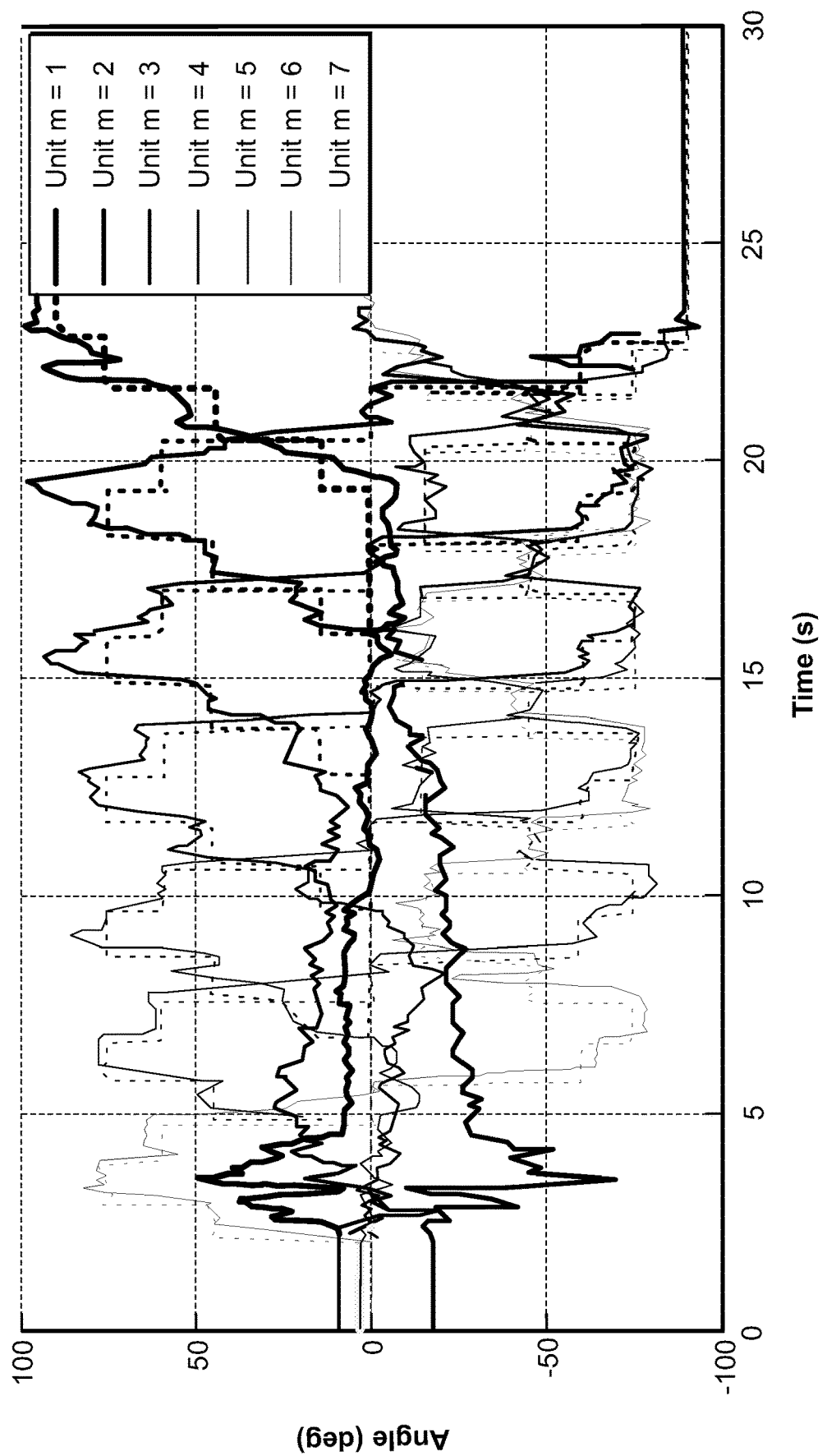

A simplified path that emulates the turns in a colon is also analyzed for the follow-the-leader path planning algorithm. A simple phantom is used to measure repeatability, contact forces, and conformation. FIG. 10A consists of snapshots of the robot in follow-the-leader mode as it traverses the path illustrated in FIG. 4 that emulates the turns in the colon. Different parts of the colon are highlighted in pink. FIG. 10B illustrates time-series data of both the desired bending angles (dotted lines) and measured closed loop bending angles (solid lines) for each of the seven bending segments. Because all bending segments not within the field of view are left uncontrolled, there are large errors especially for units m=1 and m=2 for times less than 15 seconds in FIG. 10B. The robot replicates the desired shape shown in FIG. 4 which is made up of four turns each of 90 degrees in magnitude. The robot transmits much of the insertion resistance down to the endoscope outside the field of view.

Figure 11A:
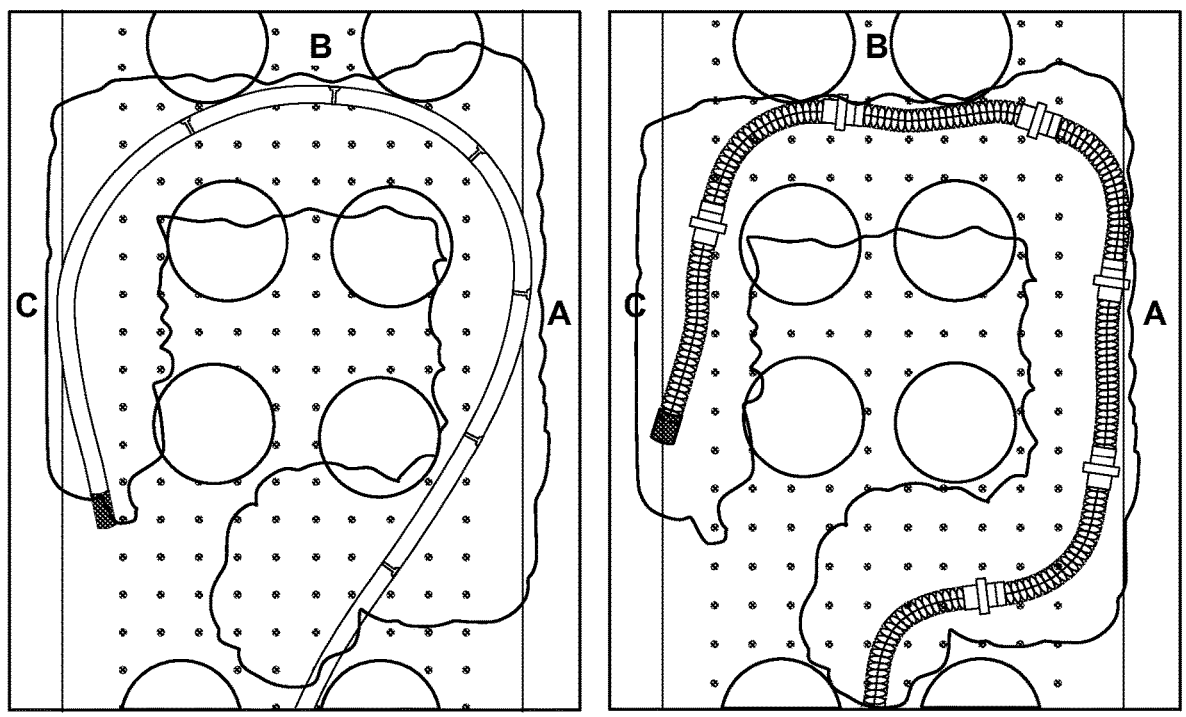
FIG. 11A illustrates the conformations of an Olympus CF-IBW endoscope and an exemplary continuum robotic endoscope as described herein.

More rigid closed loop bending segments transmit more of the forces through the body of the robot and reduce forces exerted on the side walls when the robot changes direction. However, a lower stiffness actually improves the ability of the robot to follow a constrained path, reducing the path errors shown in FIG. 4 and preventing accidental colon wall perforation. A comparison of forces exerted on the walls of the setup are shown in Table I of FIG. 11B for an Olympus CF-IBW conventional endoscope and a robotic endoscope according to various embodiments. Snapshots of the conventional and robotic endoscopes are shown in FIG. 11A. The normal forces exerted by the endoscopes on the walls are measured at three points A, B and C. Five different tests were conducted for each endoscope and the maximum forces during those tests were collected from each contact point. The means and standard deviations are shown in the table. The maximum forces exerted on the walls of the setup are measured when the endoscopes are allowed to smoothly slide along all the walls. The forces exerted on the walls of the setup are due to several factors including the forces required to change the shape of the endoscope, forces required to move the mass of the endoscope, and forces due to friction. In general, the maximum forces occur at the conformation shown in FIG. 11A. The contributions to the forces exerted on the wall at point A include the additional mass of the endoscope as well as the additional forces from sliding friction at points B and C. Therefore, the forces are generally larger at point A than the other points.

The conventional endoscope exerts more force on the external walls (at statistically significant levels; $p<4.5\times10^{-5}$) when attempting to reach the desired shape because the body of the endoscope cannot make independent bends. The conventional endoscope is stiffer, and larger force is required to change the shape of the endoscope. The mass of the conventional endoscope is also higher at 0.320 kg for a length of 910 mm. These factors contribute to the higher forces in Table I. The robotic endoscope can change shape thereby virtually eliminating the forces required to change its conformation. In some cases, the robotic endoscope does not contact wall C. The robotic endoscope is also lighter, reducing the forces exerted on the colon walls.

Repeatability data can also be obtained for these two motions. It is important to note that the robotic endoscope is designed to be flexible (to avoid puncturing the colon walls) and to operate in conjunction with a human operator's motions (such as insertion during a follow-the-leader path plan), and therefore position repeatability is not paramount. Here, fields are designed to be relatively open and prevent the robot from relying on walls to reduce the trial-to-trial variation. Repeatability data for angle tracking from gyroscope readings is shown in Table II of FIG. 11B. The steady state tracking errors from the desired path are collected from each measurement, and the average of all seven bending segments across five independent measurements is shown in the first row. The maximum error of each measurement is also shown along with the inter-trial (or trial-to-trial) variation. This shows that the angle tracking is typically 1 to 4 degrees with the follow-the-leader path producing the largest angle tracking errors.

The corresponding positioning data from video data is shown in Table III of FIG. 11B. Each experiment was completed five times and the video data was overlapped. Four frames of interest were chosen, similar to the four frames shown in FIGS. 9A and 10A. The maximum range of the tip and body motions for those four frames are then measured. The majority of the variation for the uncoiling motion occurs towards the end of the uncoiling and is eventually corrected by utilizing the straightening algorithm. The tip tends to produce more position variation than any other point on the body. For the follow-the-leader motion, the majority of the position variation is due to the operator insertion and is highest at frame (iii). The typical position variation is 30 to 40 mm.

Figure 12:
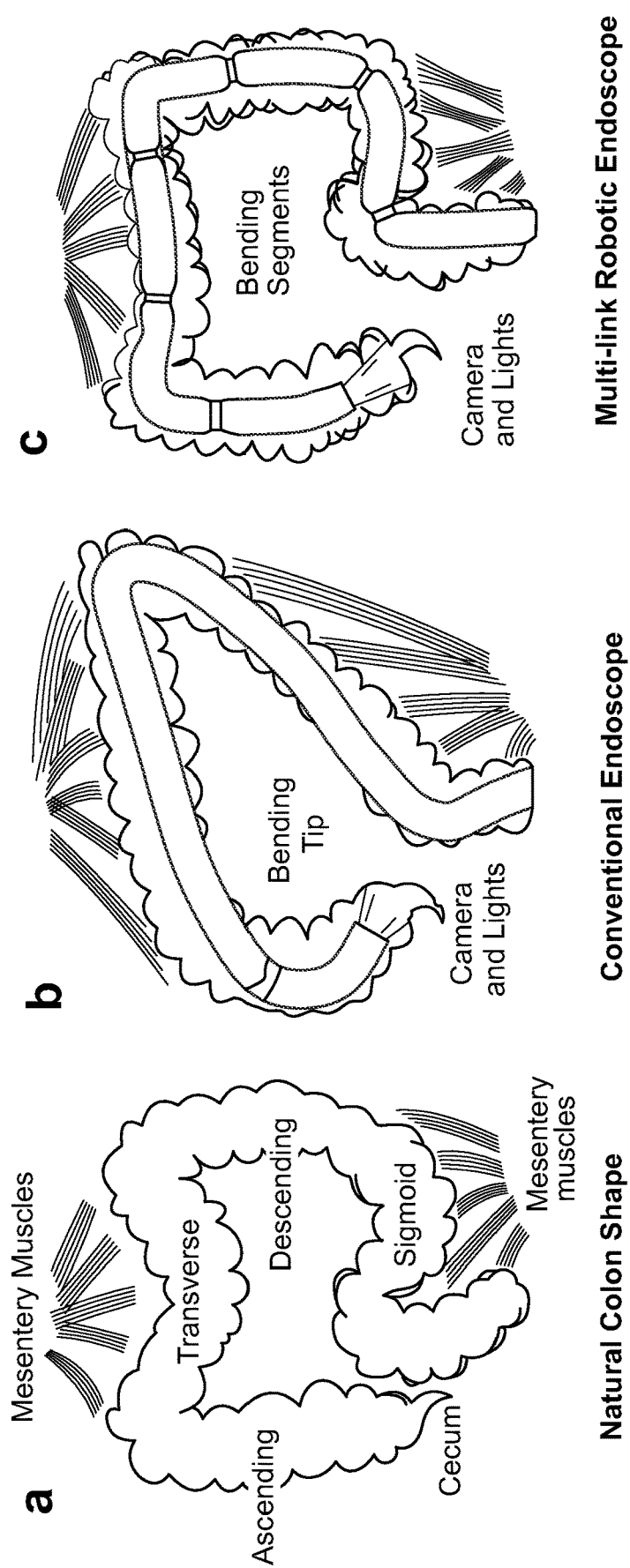
FIG. 12 illustrates the natural shape of a human colon and its shape upon the insertion of a conventional endoscope or a continuum endoscope according to various embodiments.

FIG. 12 illustrates a schematic of the human colon under several circumstances: in its natural state (a) and upon insertion of a conventional endoscope (b) or a multi-link robotic endoscope according to various embodiments (c). It is clear that the endoscope presented herein is superior in terms of allowing the colon to maintain its natural shape. By avoiding stress on the colon caused by a relatively inflexible conventional endoscope, the patient is made more comfortable and the possibility of tears, ruptures, or abrasions along the colon are reduced significantly.

Figure 13A:
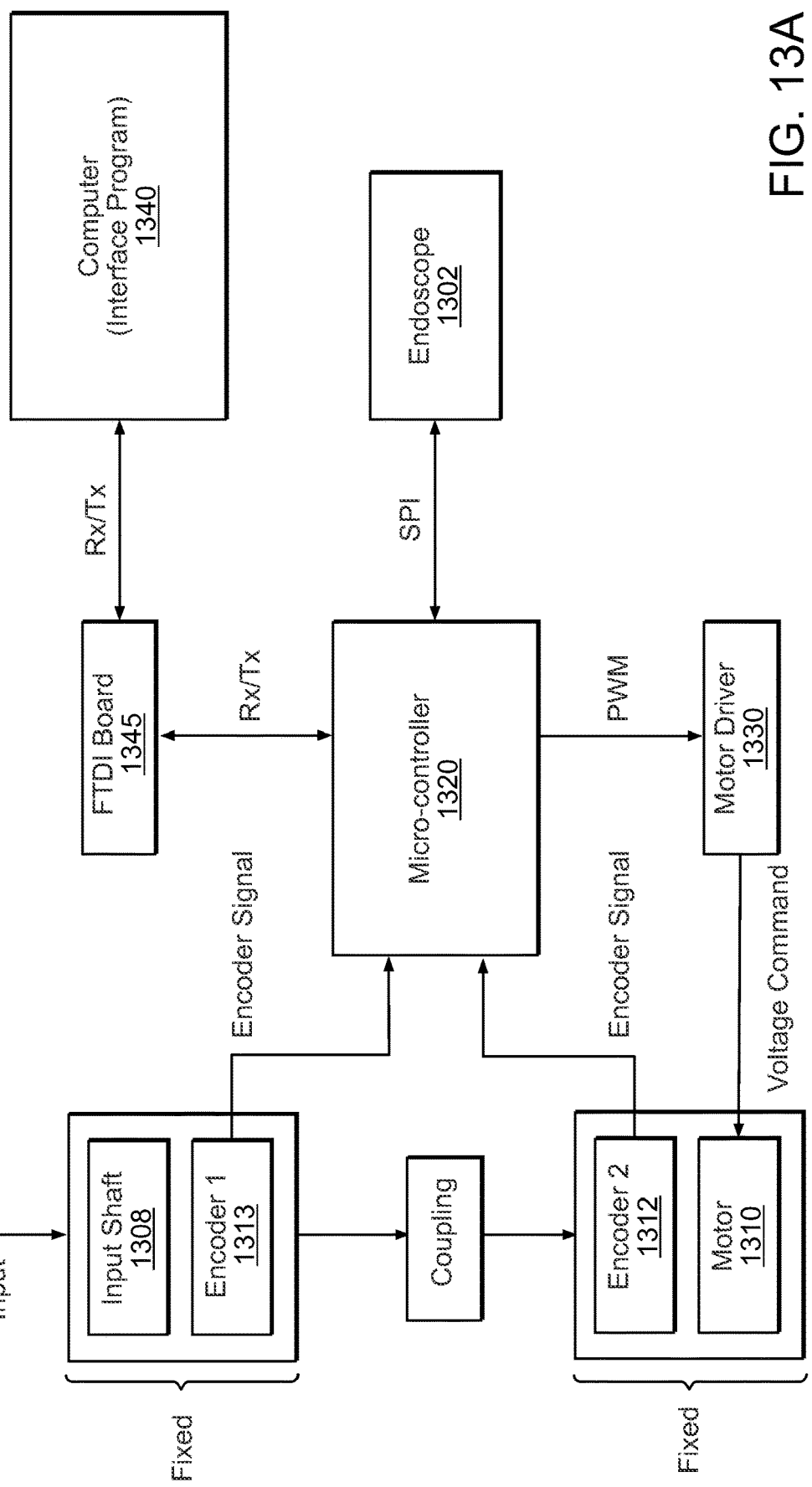
FIGS. 13A-13B illustrate a haptic feedback system for a continuum endoscope according to various embodiments.

An overview of a prototype human interface 1300 is shown in FIG. 13A. The overview shows how the robotic endoscope is to be controlled by a physician using a handheld controller. The user interface and visualization system 1300 is written in C#. The user interface 1300 has several functions. The interface has the ability to change controller settings, change visualization settings, record data, and load path commands. The raw data from the daughterboards can be graphed and the real-time visualization window can be used to show the conformation of the full robot based on the measurements made at each daughterboard of the segment controller. Because the visualization is based on measurements and not user interface commands, it is possible to move the robot by hand and see the conformation change on the screen. The visualization is useful if the robot is obstructed from view during an inspection. In some embodiments, here may be a camera video window that shows real-time video from the tip camera.

In some embodiments, a handheld controller may be used to directly control the robot. The left joystick on the handheld controller is used to control the tip segment while the right joystick can control any of the remaining segments by selecting the unit with the D-pad. The selected unit change color on the visualization screen and the LED for that unit lights up. The handheld interface can be used to change visualization settings and to calibrate the sensors. There are also several macros that can be set with the buttons and triggers on the controller including extending, retracting, and straightening the robot. More complex preplanned paths can be executed directly by the user interface. The tactile vibration on the controller is used to send warnings to the user indicating if the robot is over-rotated or if there are other faults.

In another embodiment of the control system for one haptic control handle, a user 1305 provides input via an input shaft 1308. Encoder 1 1313 is coupled to a motor 1310 and Encoder 2 1312. Both encoders 1312, 1313 send encoder signals to a microcontroller 1320. A motor driver 1330 sends voltage commands to the motor 1310. The microcontroller 1320 is in communication with an FTDI board 1345 which is in further communication with the interface program on a computer 1340. The microcontroller controls the motor drive 1330 with pulse-width modulation signals and is connected to the endoscope 1302 via the serial peripheral interface.

Figure 13B:
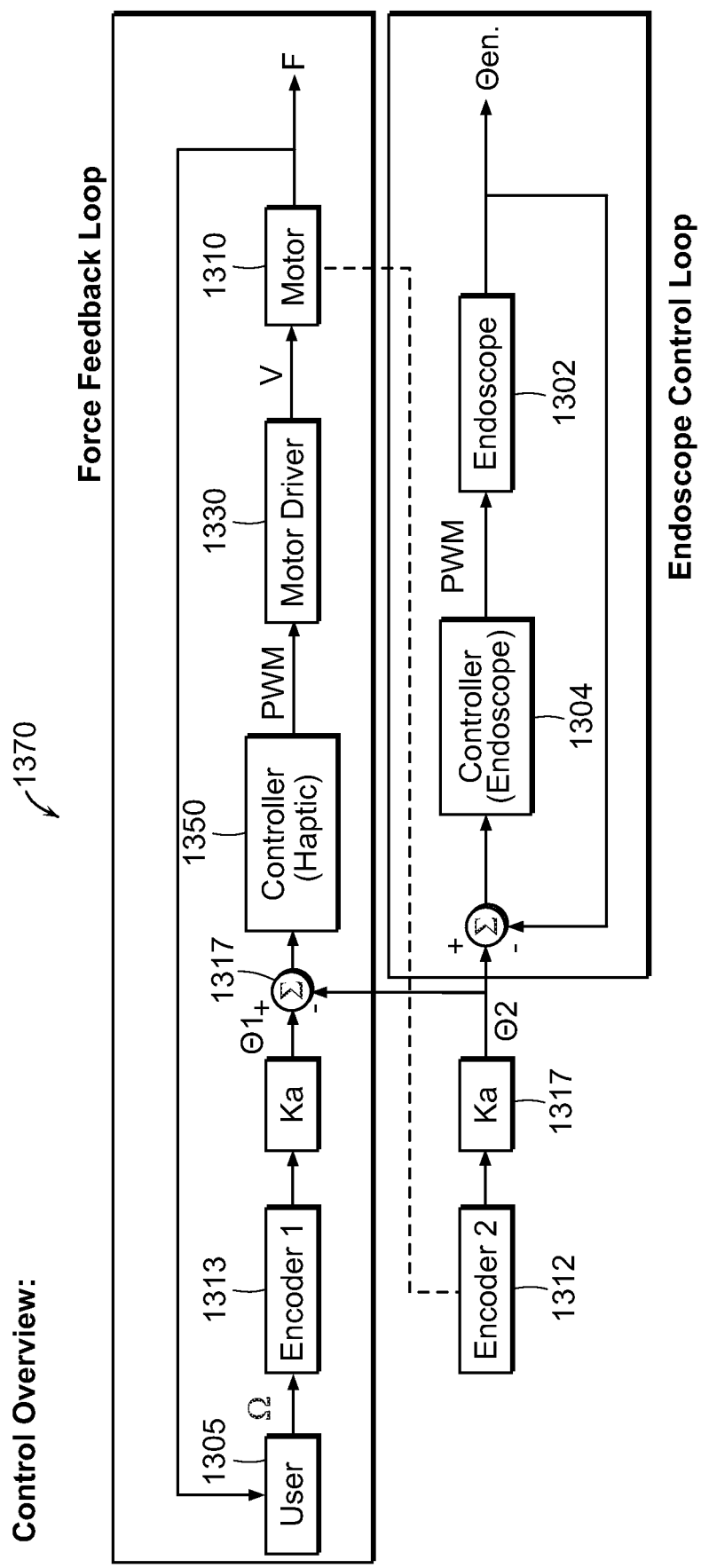

In order for a user 1305 to sense the forces exerted at the joints of the endoscope during a procedure, a haptic system 1370 is necessary. The haptic human interface handle prototype may be used so that the user 1305 can manipulate a wheel to control one axis of one unit in the endoscope. An example of a possible embodiment of the control system is shown in FIG. 13B. As the user 1305 turns the handle, the signal is read by the top encoder (Encoder 1) 1313 and part of the force is transferred through a soft, flexible coupling to a second encoder (Encoder 2) 1312. These signals are subtracted 1317 and the difference between the two is scaled to represent a difference in force. This information is sent to the user-side haptic controller 1350, which drives the motor 1310 on the bottom. The motor position read, for example, by Encoder 2 1312 matches the angle that the endoscope tip has tried to achieve using its own feedback loop.

If the endoscope tip's position is hindered by contact with the wall, it will be unable to achieve the desired position set by the user and will produce a force on the colon wall. Ideally in haptic systems, we would like to also produce a force on the user's handle to simulate the force produced by the endoscope tip on the colon wall. In this system, the motor 1310 in the haptic system tracks the angle that the endoscope tip is currently at even though the user's desired angle is larger. This means that Encoder 1 1313 and Encoder 2 1312 are at different positions, which allows the soft coupling to bend. This causes the user to feel a torsional force caused by the angle difference thereby allowing the user to "feel" the endoscope tip force as it contacts the colon wall. Using 2 handles, the haptic feedback for both rotational axes can be integrated on one endoscope unit. Using multiple control handles or a set of "select" buttons, we can go through the different units of the endoscope to provide the user with haptic feedback on each separate joint.

This haptic feedback system is unique and utilizes a soft coupling to provide force feedback rather than directly using force sensors. Other possible embodiments can use the motor voltage at the endo scope tip as a metric for force output. Force limiting can also be implemented on the endoscope tip by limiting the output position. At the same time, a warning signal (a mechanical buzz, a light, and/or a sound) can be provided to the user if the endoscope tip is pressing with a force on the colon wall that is greater than a certain threshold that represents a force less than a perforation force.

Figure 14A:
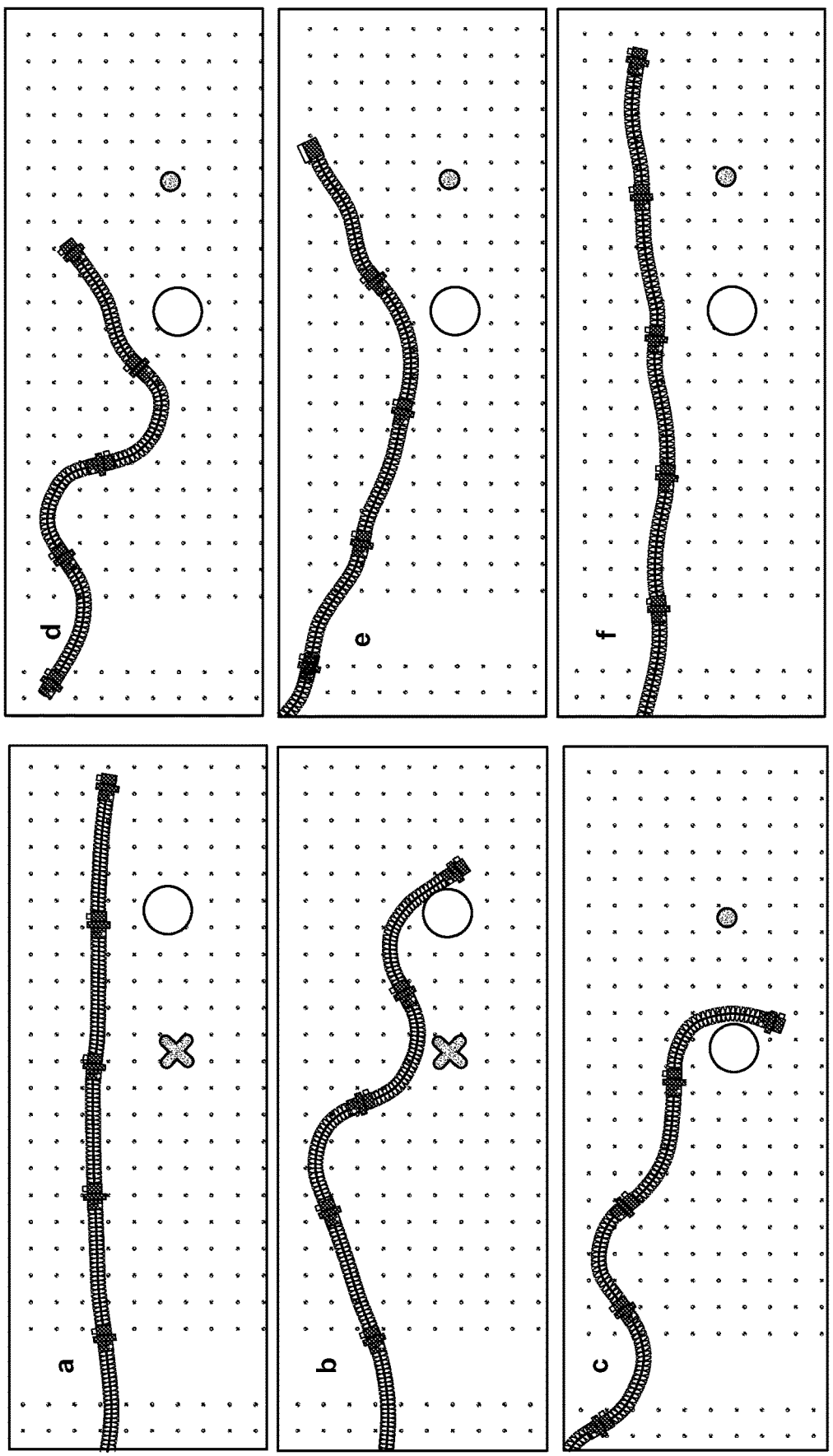
FIGS. 14A-14B illustrate additional motions that may be achieved using the robotic endoscope according to various embodiments.
Figure 14B:
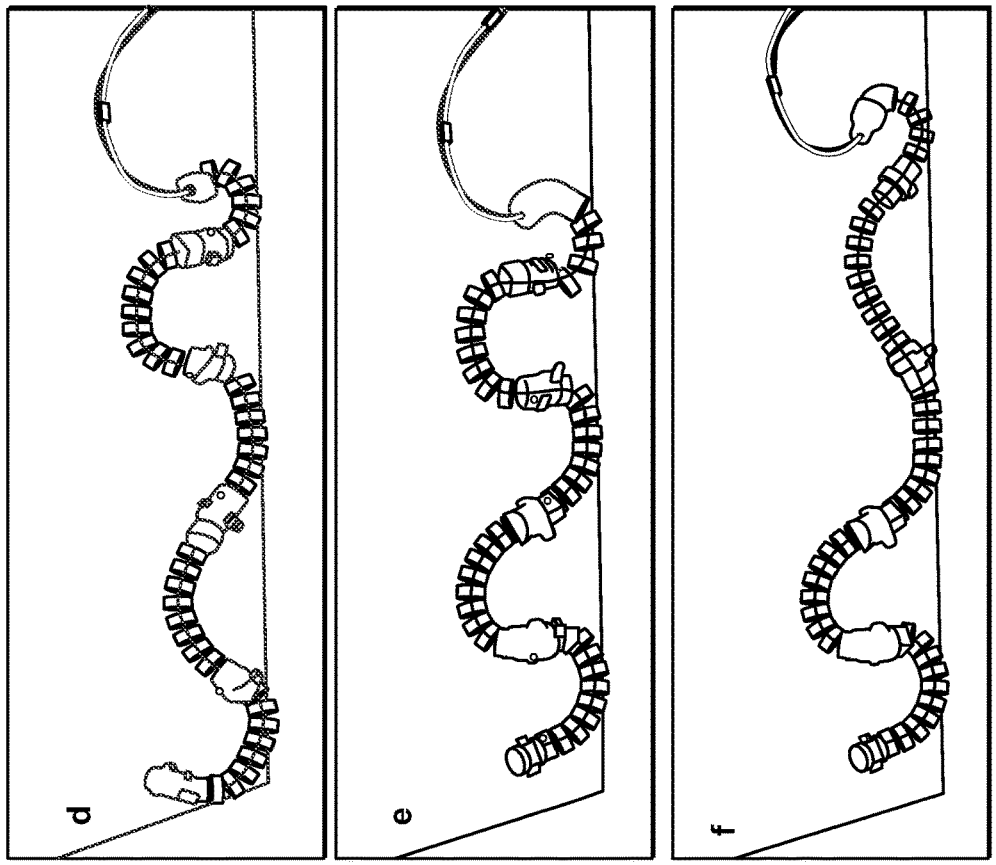
Figure 14B:
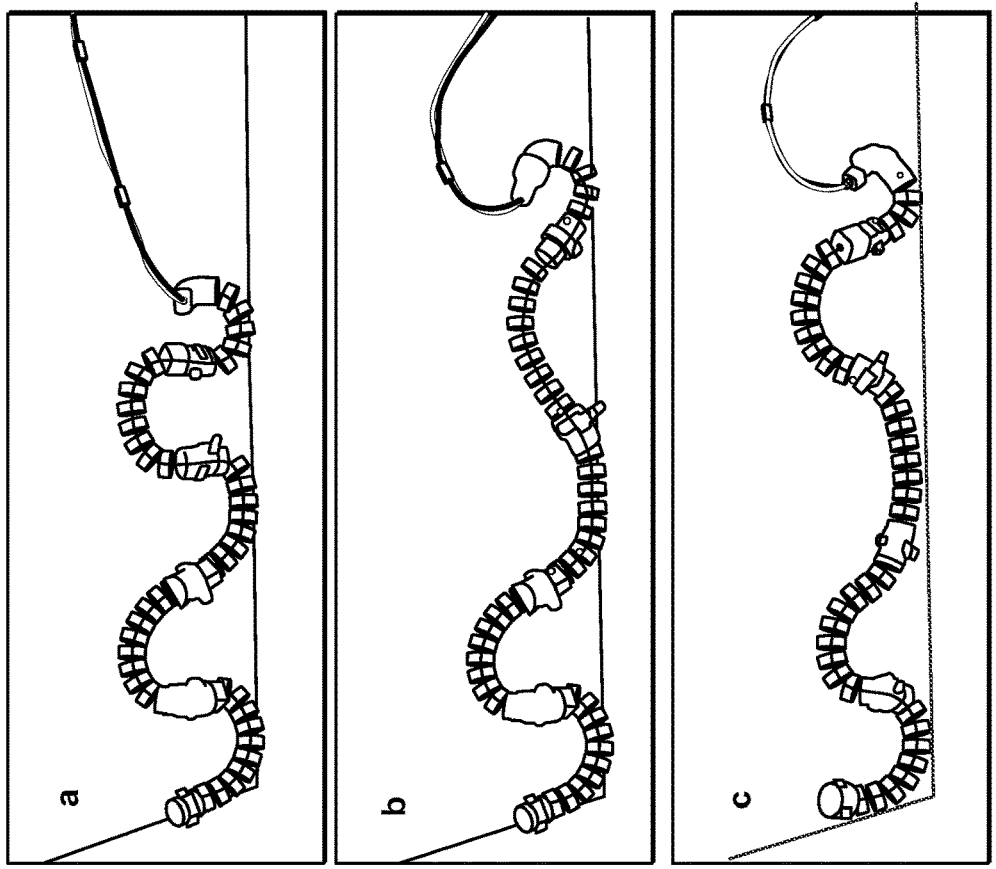

FIGS. 14A and 14B depict alternative motions that an endoscope according to various embodiments may perform. In FIG. 14A, screenshots are given that show grasping motion conducted by the endoscope. Over the course of the screenshots, the white circle is grabbed and moved from the location of the red circle to the location of the red X. This can be achieved by either hard coding in motions, by human control of each joint in sequence using macros, by using external video feedback, or by simulated path planning. The endoscope in FIG. 14B is shown performing a crawling or inch-worming motion. The robot moves different units in contact with the ground in series to inch itself forward. Two contact points are always maintained with the ground. This can be achieved by moving the front "leg" forward and contacting the ground, then lifting the middle "leg" off the ground and advancing it forward and placing it on the ground, and finally lifting and advancing the final "leg".

Figure 15:
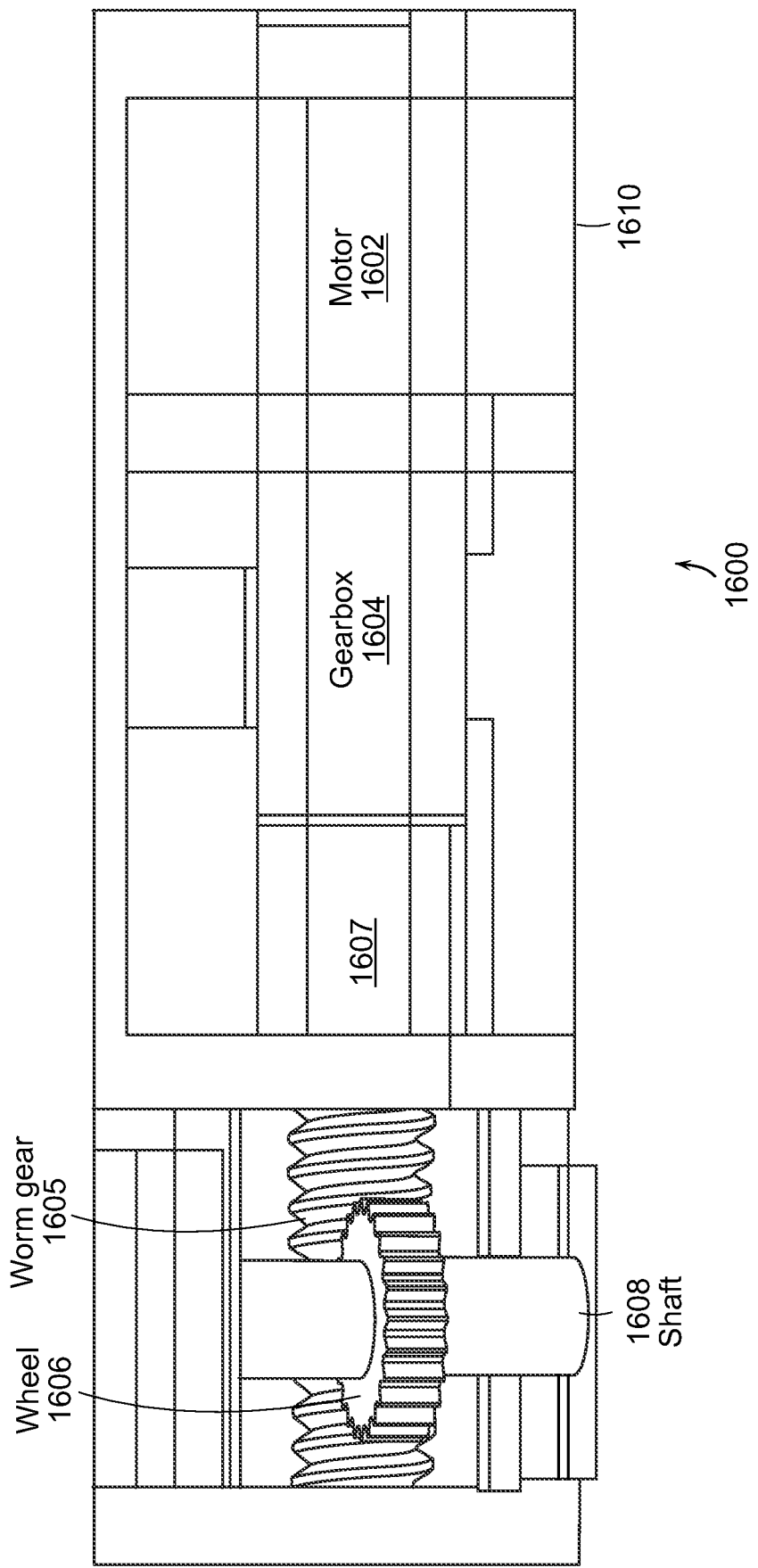
FIG. 15 illustrates another drive system for a motorized bending segment within a robotic endoscope according to various embodiments.

FIG. 15 depicts an illustrative alternative embodiment of a motor module section 1600 for such endoscopes that can be employed to increase the torque to turn an inserted biopsy tool with the rest of the endoscope. As shown in FIG. 15, the motor module section 1600 includes a motor 1602, a gearbox 1604, a worm gear 1605, a wheel 1606, and a shaft 1608. For example, the motor 1602 can be a DC motor or any other suitable type of motor, and the gearbox 1604 may be a 25:1 gearbox or any other suitable gearbox. The motor module section 1600 is operative to increase a pulling force to ease the bending of a stiffened scope.

As further shown in FIG. 15, an output shaft 1607 of the motor 1602 and the gearbox 1604 is coupled to the worm gear 1605, which drives a worm wheel 1606, and causes rotation of the shaft 1608. For example, the reduction of the worm assembly including the worm gear 1605 and the wheel 1606 can be 23:1, or any other suitable ratio. In accordance with the illustrative embodiment of FIG. 15, the gear train results in a total 575:1 gear reduction. Such a reduction can supply sufficient torque to pull a stiffened scope and a biopsy tool. A stiff motor module 1610 surrounds and holds the motor 1602, and bears the worm gear 1605. It is noted that brass bearings can be added for the tip of the worm gear 1605 and the shaft 1608, and that E-clips can be used to constrain the shaft 1608 to rotation only.

Figure 16:
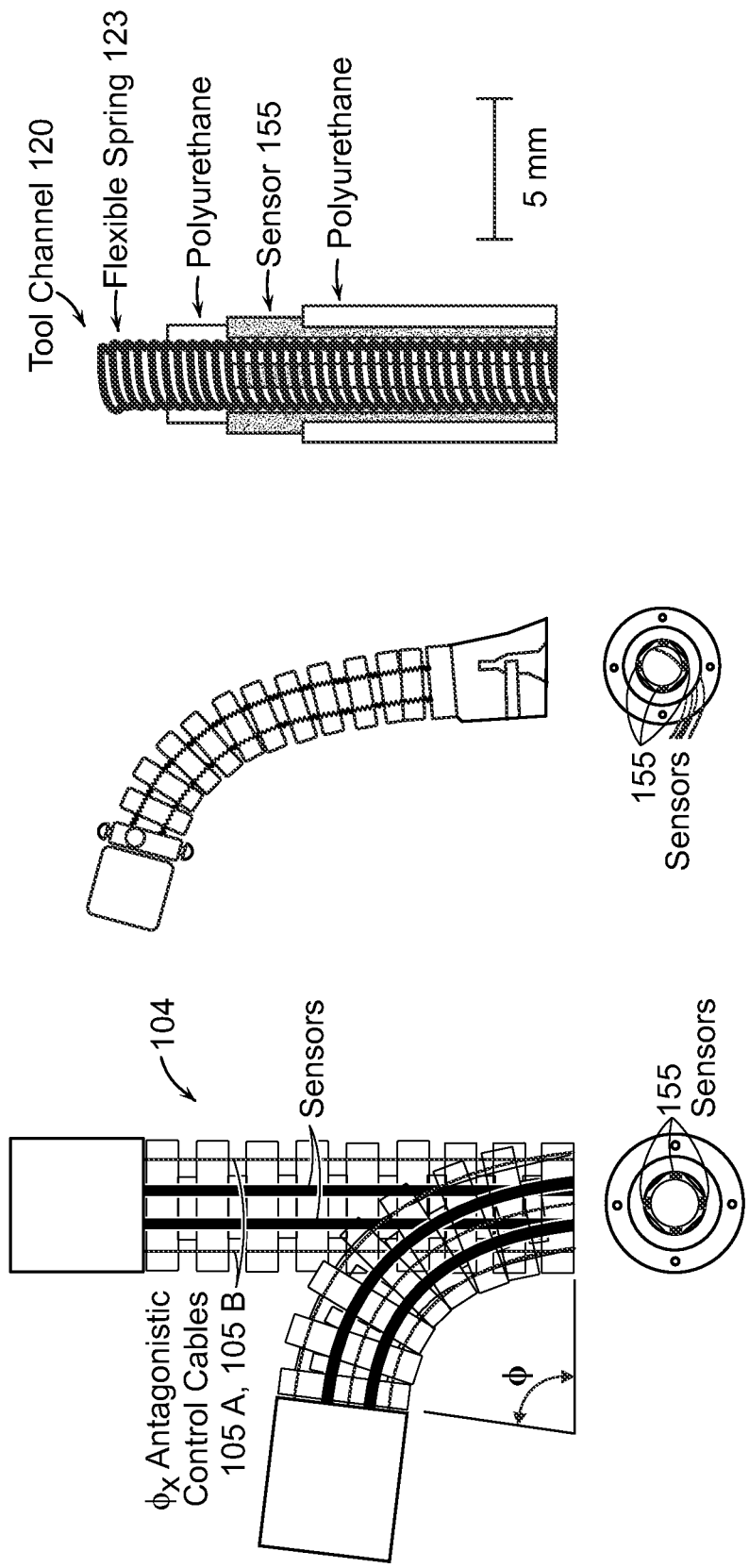
FIG. 16 illustrates a bending segment fitted with a force or strain sensor according to various embodiments.

FIG. 16 shows a bending segment with an embedded force or strain sensor according to various embodiments. The strain sensors 155 can be embedded with the spring 123 that forms the tool channel 120 to provide information about the force, strain, or orientation of the bending module. As the control cables 105A-D are manipulated, the bending segment 104 bends accordingly. The force or strain sensors will detect this change and transmit signals to the control system. This information can be used to interpret the orientation of the bending segment 104 when it is out of view, and the information may also be a useful proxy for the force being applied by the segment body on the colon.

The present invention relates to a modular continuum robotic endoscope system. Instead of using large actuators at the proximal end of the endoscope, preferred embodiments are modular such that each bending segment has its own set of actuators, micro controller, gyroscope and motor drivers. These sections can be individually controlled using a communications protocol to form a scalable robotic endoscope design that does not require any large external actuators for insertion or for bending the continuum segments. Kinematic modeling is performed for the turning modules in each bending segment and two path planning algorithms for uncoiling and follow-the-leader motions are outlined and simulated. Paths were generated to penalize straight motions in order to increase the endpoint stiffness of each desired configuration. The closed loop performance of the bending segments is shown as well as the performance of the robot using waypoints generated by the path planning algorithms.

There are many possible applications for this hyper-redundant modular continuum robotic endoscope systems. In additional to medical applications of endoscopy or minimally invasive surgery, the devices of the present disclosure can be applied to other fields such as inspection (including but not limited to pipes, around corners, in rubble, or in other difficult to access locations), or in robotics (including but not limited to crawling robots and snake-like robots). Additional coordinated motions that can be useful for physicians include a more compact uncoiling algorithm, rotational scanning, grasping and propulsion modes. In particular, three-dimensional paths and more advanced phantoms that better simulate human colons can be employed with a larger number of bending segments. Additional effects such as gravity, friction, tissue contact, and folds in the colon walls can be included in the system programming.

While the present invention has been described herein in conjunction with preferred embodiments, a person of ordinary skill in the art can effect changes, substitutions or equivalents to the systems and methods described herein, which are intended to fall within the appended claims and any equivalents thereof.

The invention claimed is:

1. A modular segmented continuum endoscope comprising:
a continuum endoscope having a distal end and a plurality of connected segments extending along a length of the endoscope in sequence that are configured to be inserted into a patient to perform a surgical procedure, each segment in the plurality of connected segments having a plurality of at least three connected turning modules;
an electric drive motor module in each segment being connected to the plurality of turning modules of each respective segment and configured to control relative angular orientation of the plurality of at least three connected turning modules such that the plurality of at least three connected turning modules within each segment orient to form one of a plurality of redundant shapes having a radius of curvature for each selected segment, wherein a selected segment shape is defined at least by a force imparted by the electric drive motor module coupled to the selected segment and by a force imparted to the continuum endoscope by tissue contacting the continuum endoscope; and
a central controller that is communicatively connected to each electric drive motor module such that the radius of curvature of each segment is independently controlled with coordinated control signals transmitted to selected electric drive motor modules from the central controller during insertion of the endoscope into the patient, the control signals emitted in temporal sequence and including control signals to coil and uncoil the plurality of connected segments.

2. The endoscope of claim 1 wherein each segment comprises a distal module and a proximal module.

3. The endoscope of claim 1 wherein the electric drive motor module of a selected segment controls positioning of the plurality of at least three connected turning modules of the selected segment.

4. The endoscope of claim 1 further comprising a detector module.

5. The endoscope of claim 1 further comprising a memory that stores coded instructions to control motor module operation or operating mode instructions.

6. The endoscope of claim 1 further comprising a haptic control system including a first control handle to control a first rotational axis and a second control handle to control a second rotational axis.

7. The endoscope of claim 1 wherein each segment further comprises a segment controller that is connected to the electric drive motor module within the segment and that communicates with the central controller.

8. The endoscope of claim 1 further comprising a data processor and a display.

9. The endoscope of claim 1 wherein the plurality of connected segments comprises at least three segments, and wherein the endoscope further comprises a handle attached to a proximal segment and a flexible endoscope body that has a tubular shape sized for insertion into a colon.

10. The endoscope of claim 1 wherein the plurality of at least three connected turning modules in each segment are coupled to the electric drive motor module that is positioned along an axis of that segment and wherein the plurality of at least three connected turning modules are coupled by at least one cable or threaded rod that is actuated to rotate the plurality of at least three connected turning modules relative to the axis.

11. The endoscope of claim 1 wherein each segment is controlled independently from an adjoining segment and wherein the central controller transmits a first control command to a first electric drive motor module and a second control command to a second electric drive motor module.

12. The endoscope of claim 11 wherein each segment has an independently controlled bending motion.

13. The endoscope of claim 1 wherein each electric drive motor module comprises at least one of a worm gear assembly, two rotational stepper motors, a motor, a gearbox and/or a transmission.

14. The endoscope of claim 1 further comprising a first control element in each segment and a second control element in each segment.

15. The endoscope of claim 14 wherein the first control element comprises a first cable and the second control element comprises a second cable.

16. The endoscope of claim 1 further comprising an imaging detector, a data connector to connect a segment controller to the central controller, a position sensor, a gyroscope, an LVDS serializer, a force sensor, or a strain sensor.

17. The endoscope of claim 16 wherein the force or strain sensor is embedded on a spring.

18. The endoscope of claim 1 further comprising a tool channel.

19. The endoscope of claim 1 further comprising a surgical endoscope tool that is mountable to a distal module.

20. The endoscope of claim 1 wherein the central controller comprises a closed loop control system that controls yaw, pitch, and roll angles.

21. The endoscope of claim 1 wherein the endoscope is configured to be controlled by the central controller in a plurality of operational modes including an unbending mode, a straightening mode, a follow the leader mode and an insertion mode.

22. A method of operating a segmented modular continuum endoscope comprising:

inserting a continuum endoscope having a distal end and a plurality of connected segments that extend along a length of the endoscope in sequence into a patient to perform a surgical procedure, wherein each segment within the patient has a plurality of at least three connected turning modules connected to an electric drive motor module, the movement of each segment constrained by portions of the continuum endoscope at each end of each segment; and actuating the electric drive motor module in a selected segment of the continuum endoscope using a central controller to control a relative angular orientation of the plurality of at least three connected turning modules of the selected segment such that the electric drive motor module and the plurality of at least three connected turning modules within the selected segment orient to form one of a plurality of redundant shapes having a radius of curvature for the selected segment, wherein the selected segment shape is defined at least by a force imparted by the electric drive motor module coupled to the selected segment and by a force imparted to the continuum endoscope by tissue of the patient contacting the continuum endoscope, the central controller being communicatively coupled to each electric drive motor module such that the radius of curvature of each segment is independently controlled with coordinated control signals transmitted to selected electric drive motor modules from the central controller during insertion of the endoscope into the patient, the control signals emitted in temporal sequence and including control signals to coil and uncoil the plurality of connected segments.

23. The method of claim 22 wherein inserting each segment further comprises inserting a distal turning module and a proximal turning module that is connected to the electric drive motor module.

24. The method of claim 22 wherein inserting the endoscope comprises inserting at least three segments, and operating the endoscope with a handle attached to a proximal segment wherein the endoscope comprises a flexible endoscope body that has a tubular shape sized for insertion into a colon.

25. The method of claim 22 wherein the endoscope further comprises a detector module.

26. The method of claim 22 wherein the endoscope further comprises a memory that stores coded instructions to control motor module operation or operating mode instructions.

27. The method of claim 22 further comprising controlling a first rotational axis using a first handle of a haptic control system and controlling a second rotational axis using a second handle of the haptic control system.

28. The method of claim 22 wherein each electric drive motor module comprises at least one of a worm gear assembly, two rotational stepper motors, a motor, a gearbox and/or a transmission.

29. The method of claim 22 wherein each segment further comprises a segment controller that is connected to the motor module within the segment and that communicates with the central controller.

30. The method of claim 22 wherein the endoscope further comprises a data processor and a display.

31. The method of claim 22 wherein actuating each turning module in a segment that is coupled to the electric drive motor module of that segment is performed by moving at least one cable or threaded rod.

32. The method of claim 22 wherein actuating each segment is performed independently from an adjoining segment and wherein the central controller transmits a first control command to a first electric drive motor module and a second control command to a second electric drive motor module.

33. The method of claim 32 further comprising independently controlling a bending motion of each segment.

34. The method of claim 22 further comprising transmitting control signals to an electric drive motor module to actuate a first control element and a second control element.

35. The endoscope of claim 34 further comprising controlling rotation of a turning module about an axis with the first control element that comprises a first cable and the second control element that comprises a second cable.

36. The method of claim 22 further comprising imaging with at least one of an imaging detector and using a data connector to connect a segment controller to the central controller, a position sensor, a gyroscope, an LVDS serializer, a force sensor, or a strain sensor.

37. The method of claim 36 further comprising sensing data with the force or strain sensor that is embedded on a spring.

38. The method of claim 22 further comprising inserting a tool through a tool channel.

39. The method of claim 22 further comprising operating a surgical endoscope tool that is mountable to a distal module.

40. The method of claim 22 wherein the central controller operates a closed loop control system that controls yaw, pitch, and roll angles.

41. The method of claim 22 further comprising operating the endoscope using the central controller in a plurality of operational modes including an unbending mode, a straightening mode, a follow the leader mode and an insertion mode.

42. The method of claim 22 further comprising performing a surgical procedure wherein the endoscope is inserted into a colon of a patient and is steered by a user under fluoroscopic visualization to image a region of the colon.

43. A modular segmented endoscope comprising:
a continuum endoscope having a plurality of connected segments configured to be inserted into a patient to perform a surgical procedure, each segment having a plurality of at least three connected turning modules actuated by an electric drive motor module connected to a segment controller, the electric drive motor module of each segment being connected to the plurality of at least three connected turning modules of each respective segment to control relative angular orientation of the plurality of at least three connected turning modules within each segment, and
an endoscope controller connected to each segment controller, each segment controller being configured to be independently controlled with control signals from the endoscope controller such that a radius of curvature of the plurality of at least three connected turning modules of each segment can be independently controlled wherein a redundant shape of each segment is further defined in part by a force imparted to the continuum endoscope by tissue of the patient.

* * * * *